United States Patent
Au-Young et al.

(10) Patent No.: US 6,235,880 B1
(45) Date of Patent: May 22, 2001

(54) HUMAN SULFONYLUREA RECEPTOR

(75) Inventors: Janice Au-Young, Berkeley; Olga Bandman; Roger Coleman, both of Mountain View, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/208,716

(22) Filed: Dec. 9, 1998

Related U.S. Application Data

(62) Division of application No. 08/726,320, filed on Oct. 2, 1996.

(51) Int. Cl.[7] .................................................. C07K 14/705
(52) U.S. Cl. ................................................ 530/350; 514/2
(58) Field of Search ............................. 530/350, 388.22; 514/2

(56) References Cited

FOREIGN PATENT DOCUMENTS

WO 95/28411  10/1995  (WO).

OTHER PUBLICATIONS

Aguilar–Bryan et al. Cloning of the beta Cell High–Affinity Sulfonylurea Receptor: A Regulator of Insulin Secretion. Science 268:423–426, Apr. 1995.*

Atassi. Preparation of Monoclonal Antibodies to Preselected Protein Regions. Methods in Enzymology 121:69–95, 1986.*

Aguilar–Bryan, et al., "Cloning of the β Cell High–Affinity Sulfonylurea Receptor: A Regulator of Insulin Secretion, " Science, 268:423–426 (1995).

Inagaki, N., et al., "Recognition of Ikatp: An Inward Rectifier Subunit Plus the Sulfonylurea Receptor" Science, 270:1166–1170 (1995).

Inagaki, N., et al., "A Family of Sulfonylurea Receptors Determines the Pharmacological Properties of ATP–Sensitive K+ Channels" Neuron, 16:1011–1017 (1996).

Gonzalez, G., et al., (GI 1369844), GenBank Sequence Database (Accession 1369844), National Center for Biotechnology Information, National Library of Medicine, Bethesda, Maryland 20894 1998).

Philipson, L.H., et al., "Pas de Deux or More: The Sulfonylurea Receptor and K+Channels" Science, 268:372–373 (1995).

Tsui, L.C., "The spectrum of cystic fibrosis mutations" Trends Genet., 8:392 (1992).

Thomas, P.M., et al., "Mutations in the Sulfonylurea Receptor Gene in Familial Persistent Hyperinsulinemic Hypoglycemia of Infancy" Science, 268:426–429 (1995).

Amoroso, S., et al., "Glucose, Sulfonylureas, and Neurotransmitter Release: Role of ATP–Sensitive K+Channels" Science, 247:852–854 (1990).

Schmidt–Antomarchi et al., "K+channel openers activate brain sulfonylurea–sensitive K+channels and block neurosecretion" Proc. Natl. Acad. Sci., 87:3489–3492 (1990).

Fosset, M., et al., "Antidiabetic Sulfonylureas Control Action Potential Properties in Heart Cells via High Affinity Receptors That Are Linked to ATP–dependent K+Channels" J. Biol. Chem., 263:7933–7936 (1988).

Database EMBL Human Sequences, EMBL Entry: Emhum2:Hssur1rna, Jul. 16, 1996, Gonzalez, G., et al., "Human beta cell sulfonylurea receptor, SUR1, expression, ".

Thomas, P., et al., "Inactivation of the First Nucleotide–Binding Fold of the Sulfonylurea Receptor, and Familial Persistent Hyperinsulinemic Hypoglycemia of Infancy," Am. J. Hum. Genet., 59:510–518, 1996.

* cited by examiner

Primary Examiner—John Ulm
(74) Attorney, Agent, or Firm—Incyte Genomics, Inc.; Lynn E. Murry

(57) ABSTRACT

The present invention provides a human sulfonylurea receptor (SURH) and the polynucleotides which identify and encode SURH. The invention also provides genetically engineered expression vectors and host cells comprising the nucleic acid sequences encoding SURH and methods for producing the protein. The invention also provides pharmaceutical compositions containing SURH, agonists to SURH, or antagonists to SURH, and in the use of such compositions for the prevention or treatment of diseases associated with the expression of SURH. Additionally, the invention provides for the use of antisense molecules to polynucleotides encoding SURH for the treatment of diseases associated with the expression of SURH. The invention also provides diagnostic assays which utilize the polynucleotide, or fragments or the complement thereof, to hybridize to the genomic sequence or transcripts of polynucleotides encoding SURH, or anti-SURH antibodies which specifically bind to SURH.

6 Claims, 11 Drawing Sheets

```
                 10            19            28            37            46            55
5' AAT TCC CGG GTC GAC CCA CGC GTC CGC CGC GCC CGC GCC GCC ATG CCC CTG GCC
                                                          M   P   L   A 64            73            82            91           100           109
   TTC TGC GGC AGC GAG AAC CAC TCG GCC GCC TAC CGG GTG GAC CAG GGG GTC CTC
   F   C   G   S   E   N   H   S   A   A   Y   R   V   D   Q   G   V   L 118           127           136           145           154           163
   AAC AAC GGC TGC TTT GTG GAC GCG CTC AAC GTG GTG CCG CAC GTC TTC CTA CTC
   N   N   G   C   F   V   D   A   L   N   V   V   P   H   V   F   L   L 172           181           190           199           208           217
   TTC ATC ACC TTC CCC ATC CTC TTC ATT GGA TGG GGA AGT CAG AGC TCC AAG GTG
   F   I   T   F   P   I   L   F   I   G   W   G   S   Q   S   S   K   V 226           235           244           253           262           271
   CAC ATC CAC CAC AGC ACA TGG CTT CAT TTC CCT GGG CAC AAC CTG CGG TGG ATC
   H   I   H   H   S   T   W   L   H   F   P   G   H   N   L   R   W   I 280           289           298           307           316           325
   CTG ACC TTC ATG CTG CTC TTC GTC CTG GTG TGT GAG ATT GCA GAG GGC ATC CTG
   L   T   F   M   L   L   F   V   L   V   C   E   I   A   E   G   I   L 334           343           352           361           370           379
   TCT GAT GGG GTG ACC GAA TCC CAC CAT CTG CAC CTG TAC ATG CCA GCC GGG ATG
   S   D   G   V   T   E   S   H   H   L   H   L   Y   M   P   A   G   M 388           397           406           415           424           433
   GCG TTC ATG GCT GCT GTC ACC TCC GTG GTC TAC TAT CAC AAC ATC GAG ACT TCC
   A   F   M   A   A   V   T   S   V   V   Y   Y   H   N   I   E   T   S 442           451           460           469           478           487
   AAC TTC CCC AAG CTG CTA ATT GCC CTG CTG GTG TAT TGG ACC CTG GCC TTC ATC
   N   F   P   K   L   L   I   A   L   L   V   Y   W   T   L   A   F   I 496           505           514           523           532           541
   ACC AAG ACC ATC AAG TTT GTC AAG TTC TTG GAC CAC GCC ATC GGC TTC TCG CAG
   T   K   T   I   K   F   V   K   F   L   D   H   A   I   G   F   S   Q 550           559           568           577           586           595
   CTA CGC TTC TGC CTC ACA GGG CTG CTG GTG ATC CTC TAT GGG ATG CTG CTC CTC
   L   R   F   C   L   T   G   L   L   V   I   L   Y   G   M   L   L   L 604           613           622           631           640           649
   GTG GAG GTC AAT GTC ATC AGG GTG AGG AGA TAC ATC TTC TTC AAG ACA CCG AGG
   V   E   V   N   V   I   R   V   R   R   Y   I   F   F   K   T   P   R 658           667           676           685           694           703
   GAG GTG AAG CCT CCC GAG GAC CTG CAA GAC CTG GGG GTA CGC TTC CTG CAG CCC
   E   V   K   P   P   E   D   L   Q   D   L   G   V   R   F   L   Q   P
```

FIGURE 1A

```
            712          721          730          739          748          757
TTC GTG AAT CTG CTG TCC AAA GGC ACC TAC TGG TGG ATG AAC GCC TTC ATC AAG
 F   V   N   L   L   S   K   G   T   Y   W   W   M   N   A   F   I   K 766          775          784          793          802          811
ACT GCC CAC AAG AAG CCC RTC GAC TTG CGA GCC ATC GGG AAG CTG CCC ATC GCC
 T   A   H   K   K   P   X   D   L   R   A   I   G   K   L   P   I   A 820          829          838          847          856          865
ATG AGG GCC CTC ACC AAC TAC CAA CGG CTC TGC GAG GCC TTT GAC GCC CAG CGG
 M   R   A   L   T   N   Y   Q   R   L   C   E   A   F   D   A   Q   R 874          883          892          901          910          919
AAG GAC ATT CAG GGC ACT CAA GGT GCC CGG GCC ATC TGG CAG GCA CTC AGC CAT
 K   D   I   Q   G   T   Q   G   A   R   A   I   W   Q   A   L   S   H 928          937          946          955          964          973
GCC TTC GGG AGG CGC CTG GTC CTC AGC AGC ACT TTC CGC ATC TTG GCC GAC CTG
 A   F   G   R   R   L   V   L   S   S   T   F   R   I   L   A   D   L 982          991          1000         1009         1018         1027
CTG GGC TTC GCC GGG CCA CTG TGC ATC TTT GGG ATC GTG GAC CAC CTT GGG AAG
 L   G   F   A   G   P   L   C   I   F   G   I   V   D   H   L   G   K 1036         1045         1054         1063         1072         1081
GAG AAC GAC GTC TTC CAG CCC AAG ACA CAA TTT CTC GGG GTT TAC TTT GTC TCA
 E   N   D   V   F   Q   P   K   T   Q   F   L   G   V   Y   F   V   S 1090         1099         1108         1117         1126         1135
TCC CAA GAG TTC CTT GCC AAT GCC TAC GTC TTA GCT GTG CTT CTG TTC CTT GCC
 S   Q   E   F   L   A   N   A   Y   V   L   A   V   L   L   F   L   A 1144         1153         1162         1171         1180         1189
CTC CTA CTG CAA AGG ACA TTT CTG CAA GCA TCC TAC TAT GTG GCC ATT GAA ACT
 L   L   L   Q   R   T   F   L   Q   A   S   Y   Y   V   A   I   E   T 1198         1207         1216         1225         1234         1243
GGA ATT AAC TTG AGA GGA GCA ATA CAG ACC AAG ATT TAC AAT AAA ATT ATG CAC
 G   I   N   L   R   G   A   I   Q   T   K   I   Y   N   K   I   M   H 1252         1261         1270         1279         1288         1297
CTG TCC ACC TCC AAC CTG TCC ATG GGA GAA ATG ACT GCT GGA CAG ATC TGY AAT
 L   S   T   S   N   L   S   M   G   E   M   T   A   G   Q   I   C   N 1306         1315         1324         1333         1342         1351
CTG GTT GCC ATC GAC ACC AAT CAG CTC ATG TGG TTT TTC TTC TTG TGC CCA AAC
 L   V   A   I   D   T   N   Q   L   M   W   F   F   F   L   C   P   N 1360         1369         1378         1387         1396         1405
CTC TGG GCT ATG CCA GTA CAG ATC ATT GTG GGT GTG ATT CTC CTC TAC TAC ATA
 L   W   A   M   P   V   Q   I   I   V   G   V   I   L   L   Y   Y   I
```

FIGURE 1B

```
       1414         1423         1432         1441         1450         1459
CTC GGA GTC AGT GCC TTA ATT GGA GCA GCT GTC ATC ATT CTA CTG GCT CCT GTC
 L   G   V   S   A   L   I   G   A   A   V   I   I   L   L   A   P   V 1468         1477         1486         1495         1504         1513
CAG TAC TTC GTG GCC ACC AAG CTG TCT CAG GCC CAG CGG AGC ACA CTG GAG TAT
 Q   Y   F   V   A   T   K   L   S   Q   A   Q   R   S   T   L   E   Y 1522         1531         1540         1549         1558         1567
TCC AAT GAG CGG CTG AAG CAG ACC AAC GAG ATG CTC CGC GGC ATC AAG CTG CTG
 S   N   E   R   L   K   Q   T   N   E   M   L   R   G   I   K   L   L 1576         1585         1594         1603         1612         1621
AAG CTG TAC GCC TGG GAG AAC ATC TTC CGC ACG CGG GTG GAG ACG ACC CGC AGG
 K   L   Y   A   W   E   N   I   F   R   T   R   V   E   T   T   R   R 1630         1639         1648         1657         1666         1675
AAG GAG ATG ACC AGC CTC AGG GCC TTT GCC ATC TAT ACC TCC ATC TCC ATT TTC
 K   E   M   T   S   L   R   A   F   A   I   Y   T   S   I   S   I   F 1684         1693         1702         1711         1720         1729
ATG AAC ACG GCC ATC CCC ATT GCA GCT GTC CTC ATA ACT TTC GTG GGC CAT GTC
 M   N   T   A   I   P   I   A   A   V   L   I   T   F   V   G   H   V 1738         1747         1756         1765         1774         1783
AGC TTC TTC AAA GAG GCC GAC TTC TCG CCC TCC GTG GCC TTT GCC TCC CTC TCC
 S   F   F   K   E   A   D   F   S   P   S   V   A   F   A   S   L   S 1792         1801         1810         1819         1828         1837
CTC TTC CAT ATC TTG GTC ACA CCG CTG TTC CTG CTG TCC AGT GTG GTC CGA TCT
 L   F   H   I   L   V   T   P   L   F   L   L   S   S   V   V   R   S 1846         1855         1864         1873         1882         1891
ACC GTC AAA GCT CTA GTG AGC GTG CAA AAG CTA AGC GAG TTC CTG TCC AGT GCA
 T   V   K   A   L   V   S   V   Q   K   L   S   E   F   L   S   S   A 1900         1909         1918         1927         1936         1945
GAG ATC CGT GAG GAG CAG TGT GCC CCC CAT GAG CCC ACA CCT CAG GGC CCA GCC
 E   I   R   E   E   Q   C   A   P   H   E   P   T   P   Q   G   P   A 1954         1963         1972         1981         1990         1999
AGC AAG TAC CAG GCG GTG CCC CTC AGG GTT GTG AAC CGC AAG CGT CCA GCC CGG
 S   K   Y   Q   A   V   P   L   R   V   V   N   R   K   R   P   A   R 2008         2017         2026         2035         2044         2053
GAG GAT TGT CGG GGC CTC ACC GGC CCA CTG CAG AGC CTG GTC CCC AGT GCA GAT
 E   D   C   R   G   L   T   G   P   L   Q   S   L   V   P   S   A   D 2062         2071         2080         2089         2098         2107
GGC GAT GCT GAC AAC TGC TGT GTC CAG ATC ATG GGA GGC TAC TTC ACG TGG ACC
 G   D   A   D   N   C   C   V   Q   I   M   G   G   Y   F   T   W   T
```

FIGURE 1C

```
       2116          2125          2134          2143          2152          2161
CCA GAT GGA ATC CCC ACA CTG TCC AAC ATC ACC ATT CGT ATC CCC CGA GGC CAG
 P   D   G   I   P   T   L   S   N   I   T   I   R   I   P   R   G   Q 2170          2179          2188          2197          2206          2215
CTG ACT ATG ATC GTG GGG CAG GTG GGC TGC GGC AAG TCC TCG CTC CTT CTA GCC
 L   T   M   I   V   G   Q   V   G   C   G   K   S   S   L   L   L   A 2224          2233          2242          2251          2260          2269
GCA CTG GGG GAG ATG CAG AAG GTC TCA GGG GCT GTC TTC TGG AGC AGC AGC CTT
 A   L   G   E   M   Q   K   V   S   G   A   V   F   W   S   S   S   L 2278          2287          2296          2305          2314          2323
CCT GAC AGC GAG ATA GGA GAG GAC CCC AGC CCA GAG CGG GAG ACA GCG ACC GAC
 P   D   S   E   I   G   E   D   P   S   P   E   R   E   T   A   T   D 2332          2341          2350          2359          2368          2377
TTG GAT ATC AGG AAG AGA GGC CCC GTG GCC TAT GCT TCG CAG AAA CCA TGG CTG
 L   D   I   R   K   R   G   P   V   A   Y   A   S   Q   K   P   W   L 2386          2395          2404          2413          2422          2431
CTA AAT GCC ACT GTG GAG GAG AAC ATC ATC TTT GAG AGT CCC TTC AAC AAA CAA
 L   N   A   T   V   E   E   N   I   I   F   E   S   P   F   N   K   Q 2440          2449          2458          2467          2476          2485
CGG TAC AAG ATG GTC ATT GAA GCC TGC TCT CTG CAG CCA GAC ATC GAC ATC CTG
 R   Y   K   M   V   I   E   A   C   S   L   Q   P   D   I   D   I   L 2494          2503          2512          2521          2530          2539
CCC CAT GGA GAC CAG ACC CAG ATT GGG GAA CGG GGC ATC AAC CTG TCT GGT GGT
 P   H   G   D   Q   T   Q   I   G   E   R   G   I   N   L   S   G   G 2548          2557          2566          2575          2584          2593
CAA CGC CAG CGA ATC AGT GTG GCC CGA GCC CTC TAC CAG CAC GCC AAC GTT GTC
 Q   R   Q   R   I   S   V   A   R   A   L   Y   Q   H   A   N   V   V 2602          2611          2620          2629          2638          2647
TTC TTG GAT GAC CCC TTC TCA GCT CTG GAT ATC CAT CTG AGT GAC CAC TTA ATG
 F   L   D   D   P   F   S   A   L   D   I   H   L   S   D   H   L   M 2656          2665          2674          2683          2692          2701
CAG GCC GGC ATC CTT GAG CTG CTC CGG GAC GAC AAG AGG ACA GTG GTC TTA GTG
 Q   A   G   I   L   E   L   L   R   D   D   K   R   T   V   V   L   V 2710          2719          2728          2737          2746          2755
ACC CAC AAG CTA CAG TAC CTG CCC CAT GCA GAC TGG ATC ATT GCC ATG AAG GAT
 T   H   K   L   Q   Y   L   P   H   A   D   W   I   I   A   M   K   D 2764          2773          2782          2791          2800          2809
GGC ACC ATC CAG AGG GAG GGT ACC TCA AGG ACT TCC AGA GGT CTG AAT GCC AGC
 G   T   I   Q   R   E   G   T   S   R   T   S   R   G   L   N   A   S
```

FIGURE 1D

```
       2818        2827        2836        2845        2854        2863
TCT TTG AGC ACT GGA AGA CCT CAT GAA CCG ACA GGA CCA AGA GCT GGA GAA GGA
 S   L   S   T   G   R   P   H   E   P   T   G   P   R   A   G   E   G 2872        2881        2890        2899        2908        2917
AAT GTC ACA GAG AGA AAA GCC ACA GAG CCA CCC AGG GCC TAT CTC GTG CCA TGT
 N   V   T   E   R   K   A   T   E   P   P   R   A   Y   L   V   P   C 2926        2935        2944        2953        2962        2971
CCT CGA AGG GAT GGC CTT CTG CAG GAT GAG GAA GAG GAG GAA GAG GAG GCA GCT
 P   R   R   D   G   L   L   Q   D   E   E   E   E   E   E   E   A   A 2980        2989        2998        3007        3016        3025
GAG AAC GAG GAG GAT GAC TAC CTG TCG TCC ATG CTG CAC CAG CGT GCT GAG ATC
 E   N   E   E   D   D   Y   L   S   S   M   L   H   Q   R   A   E   I 3034        3043        3052        3061        3070        3079
CCA TGG CGA GCC TGC NCC AAG TAC CTG TCC TCC GCC GGC ATC CTG CTC CTG TCG
 P   W   R   A   C   X   K   Y   L   S   S   A   G   I   L   L   L   S 3088        3097        3106        3115        3124        3133
TTG CTG GTC TTC TCA CAG CTG CTC AAG CAC ATG GTC CTG GTG GCC ATC GAC TAC
 L   L   V   F   S   Q   L   L   K   H   M   V   L   V   A   I   D   Y 3142        3151        3160        3169        3178        3187
TGG CTG GCC AAG TGG ACC GAC AGC GCC CTG ACC CTG ACC CCT GCA ACC AGG AAC
 W   L   A   K   W   T   D   S   A   L   T   L   T   P   A   T   R   N 3196        3205        3214        3223        3232        3241
TGC TCC CTC AAC CAG GAG TGC ACC CTC AAC CAG ACT GTC TAT GCC TTG GTG TTC
 C   S   L   N   Q   E   C   T   L   N   Q   T   V   Y   A   L   V   F 3250        3259        3268        3277        3286        3295
ACG GTG CTC TGC AGC CTG GGC ATT GTG CTG TGC CTC GTC ACG TCT GTC ACT GTG
 T   V   L   C   S   L   G   I   V   L   C   L   V   T   S   V   T   V 3304        3313        3322        3331        3340        3349
GAG TGG ACA GGG CTG AAG GTG GCC AAG AGA CTG CAC CGC AGC CTG CTA AAC CGG
 E   W   T   G   L   K   V   A   K   R   L   H   R   S   L   L   N   R 3358        3367        3376        3385        3394        3403
ATC ATC CTA GCC CCC ATG AGG TTT TTT GAG ACC ACG CCC CTT GGG AGC ATC CTG
 I   I   L   A   P   M   R   F   F   E   T   T   P   L   G   S   I   L 3412        3421        3430        3439        3448        3457
AAC AGA TTT TCA TCT GAC TGT AAC ACC ATC GAC CAG CAC ATC CCA TCC ACG CTG
 N   R   F   S   S   D   C   N   T   I   D   Q   H   I   P   S   T   L 3466        3475        3484        3493        3502        3511
GAG TGC CTG AGC CGC TCC ACC CTG CTC TGT GTC TCA GCC CTG GCC GTC ATC TCC
 E   C   L   S   R   S   T   L   L   C   V   S   A   L   A   V   I   S
```

FIGURE 1E

```
          3520           3529           3538           3547           3556           3565
TAT GTC ACA CCT GTG TTC CTC GTG GCC CTC TTG CCC CTG GCC ATC GTG TGC TAC
 Y   V   T   P   V   F   L   V   A   L   L   P   L   A   I   V   C   Y 3574           3583           3592           3601           3610           3619
TTC ATC CAG AAG TAC TTC CGG GTG GCG TCC AGG GAC CTG CAG CAG CTG GAT GAC
 F   I   Q   K   Y   F   R   V   A   S   R   D   L   Q   Q   L   D   D 3628           3637           3646           3655           3664           3673
ACC ACC CAG CTT CCA CTT CTC TCA CAC TTT GCC GAA ACC GTA GAA GGA CTC ACC
 T   T   Q   L   P   L   L   S   H   F   A   E   T   V   E   G   L   T 3682           3691           3700           3709           3718           3727
ACC ATC CGG GCC TTC AGG TAT GAG GCC CGG TTC CAG CAG AAG CTT CTC GAA TAC
 T   I   R   A   F   R   Y   E   A   R   F   Q   Q   K   L   L   E   Y 3736           3745           3754           3763           3772           3781
ACA GAC TCC AAC AAC ATT GCT TCC CTC TTC CTC ACA GCT GCC AAC AGA TGG CTG
 T   D   S   N   N   I   A   S   L   F   L   T   A   A   N   R   W   L 3790           3799           3808           3817           3826           3835
GAA GTC CGA ATG GAG TAC ATC GGT GCA TGT GTG GTG CTC ATC GCA GCG GTG ACC
 E   V   R   M   E   Y   I   G   A   C   V   V   L   I   A   A   V   T 3844           3853           3862           3871           3880           3889
TCC ATC TCC AAC TCC CTG CAC AGA GAG CTC TCT GCT GGC CTG GTG GGC CTG GGC
 S   I   S   N   S   L   H   R   E   L   S   A   G   L   V   G   L   G 3898           3907           3916           3925           3934           3943
CTT ACC TAC GCC CTA ATG GTC TCC AAC TAC CTC AAC TGG ATG GTG AGG AAC CTG
 L   T   Y   A   L   M   V   S   N   Y   L   N   W   M   V   R   N   L 3952           3961           3970           3979           3988           3997
GCA GAC ATG GAG CTC CAG CTG GGG GCT GTG AAG CGC ATC CAT GGG CTC CTG AAA
 A   D   M   E   L   Q   L   G   A   V   K   R   I   H   G   L   L   K 4006           4015           4024           4033           4042           4051
ACC GAG GCA GAG AGC TAC GAG GGG CTC CTG GCA CCA TCG CTG ATC CCA AAG AAC
 T   E   A   E   S   Y   E   G   L   L   A   P   S   L   I   P   K   N 4060           4069           4078           4087           4096           4105
TGG CCA GAC CAA GGG AAG ATC CAG ATC CAG AAC CTG AGC GTG CGC TAC GAC AGC
 W   P   D   Q   G   K   I   Q   I   Q   N   L   S   V   R   Y   D   S 4114           4123           4132           4141           4150           4159
TCC CTG AAG CCG GTG CTG AAG CAC GTC AAT GCC CTC ATC TCC CCT GGA CAG AAG
 S   L   K   P   V   L   K   H   V   N   A   L   I   S   P   G   Q   K 4168           4177           4186           4195           4204           4213
ATC GGG ATC TGC GGC CGC ACC GGC AGT GGG AAG TCC TCC TTC TCT CTT GCC TTC
 I   G   I   C   G   R   T   G   S   G   K   S   S   F   S   L   A   F
```

FIGURE 1F

```
        4222            4231            4240            4249            4258            4267
TTC CGC ATG GTG GAC ACG TTC GAA GGG CAC ATC ATC ATT GAT GGC ATT GAC ATC
 F   R   M   V   D   T   F   E   G   H   I   I   I   D   G   I   D   I 4276            4285            4294            4303            4312            4321
GCC AAA CTG CCG CTG CAC ACC CTG CGC TCA CGC CTC TCC ATC ATC CTG CAG GAC
 A   K   L   P   L   H   T   L   R   S   R   L   S   I   I   L   Q   D 4330            4339            4348            4357            4366            4375
CCC GTC CTC TTC AGC GGC ACC ATC CGA TTT AAC CTG GAC CCT GAG AGG AAG TGC
 P   V   L   F   S   G   T   I   R   F   N   L   D   P   E   R   K   C 4384            4393            4402            4411            4420            4429
TCA GAT AGC ACA CTG TGG GAG GCC CTG GAA ATC GCC CAG CTG AAG CTG GTG GTG
 S   D   S   T   L   W   E   A   L   E   I   A   Q   L   K   L   V   V 4438            4447            4456            4465            4474            4483
AAG GCA CTG CCA GGA GGC CTC GAT GCC ATC ATC ACA GAA GGC GGG GAG AAT TTC
 K   A   L   P   G   G   L   D   A   I   I   T   E   G   G   E   N   F 4492            4501            4510            4519            4528            4537
AGC CAG GGA CAG AGG CAG CTG TTC TGC CTG GCC CGG GCC TTC GTG AGG AAG ACC
 S   Q   G   Q   R   Q   L   F   C   L   A   R   A   F   V   R   K   T 4546            4555            4564            4573            4582            4591
AGC ATC TTC ATC ATG GAC GAG GCC ACG GCT TCC ATT GAC ATG GCC ACG GAA AAC
 S   I   F   I   M   D   E   A   T   A   S   I   D   M   A   T   E   N 4600            4609            4618            4627            4636            4645
ATC CTC CAA AAG GTG GTG ATG ACA GCC TTC GCA GAC CGC ACT GTG GTC ACC ATC
 I   L   Q   K   V   V   M   T   A   F   A   D   R   T   V   V   T   I 4654            4663            4672            4681            4690            4699
GCG CAT CGA GTG CAC ACC ATC CTG AGT GCA GAC CTG GTG ATC GTC CTG AAG CGG
 A   H   R   V   H   T   I   L   S   A   D   L   V   I   V   L   K   R 4708            4717            4726            4735            4744            4753
GGT GCC ATC CTT GAG TTC GAT AAG CCA GAG AAG CTG CTC AGC CGG AAG GAC AGC
 G   A   I   L   E   F   D   K   P   E   K   L   L   S   R   K   D   S 4762            4771            4780            4789            4798            4807
GTC TTC GCC TCC TTC GTC CGT GCA GAC AAG TGA CCT GCC AGA GCC CAA GTG CCA
 V   F   A   S   F   V   R   A   D   K 4816            4825            4834            4843            4852            4861
TCC CAC ATT CGG ACC CTG CCC ATA CCC CTG CCT GGG TTT TCT AAC TGT AAA TCA 4870            4879            4888            4897            4906            4915
CTT GTA AAT AAA TAG ATT TGA TTA TTA AAA AAA AAA AAA AAA AAA AAA AAA AAA

4924
AAA AAA AAA AAA AAA A 3'
```

FIGURE 1G

| | | |
|---|---|---|
| 1 | M P L A F C G S E N H S A A Y R V D Q G V L N N G C F V D A L | SURH |
| 1 | M P L A F C G S E N H S A A Y R V D Q G V L N N G C F V D V L | GI 1369844 |
| 1 | M P L A F C G T E N H S A A Y R V D Q G V L N N G C F V D A L | GI 1311534 |
| 1 | M P L A F C G T E N H S A A Y R V D Q G V L N N G C F V D A L | GI 784874 |
| 32 | N V V P H V F L L F I T F P I L F I G W G S Q S S K V H I H H | SURH |
| 32 | N V V P H V F L L F I T F P I L F I G W G S Q S S K V H I H H | GI 1369844 |
| 32 | N V V P H V F L L F I T F P I L F I G W G S Q S S K V H I H H | GI 1311534 |
| 32 | N V V P H V F L L F I T F P I L F I G W G S Q S S K V H I H H | GI 784874 |
| 63 | S T W L H F P G H N L R W I L T F M L L F V L V C E I A E G I | SURH |
| 63 | S T W L H F P G H N L R W I L T F M L L F V L V C E I A E G I | GI 1369844 |
| 63 | S T W L H F P G H N L R W I L T F I L L F V L V C E I A E G I | GI 1311534 |
| 63 | S T W L H F P G H N L R W I L T F I L L F V L V C E I A E G I | GI 784874 |
| 94 | L S D G V T E S H H L H L Y M P A G M A F M A A V T S V V Y Y | SURH |
| 94 | L S D G V T E S H H L H L Y M P A G M A F M A A V T S V V Y Y | GI 1369844 |
| 94 | L S D G V T E S R H L H L Y M P A G M A F M A A I T S V V Y Y | GI 1311534 |
| 94 | L S D G V T E S R H L H L Y M P A G M A F M A A I T S V V Y Y | GI 784874 |
| 125 | H N I E T S N F P K L L I A L L V Y W T L A F I T K T I K F V | SURH |
| 125 | H N I E T S N F P K L L I A L L V Y W T L A F I T K T I K F V | GI 1369844 |
| 125 | H N I E T S N F P K L L I A L L I Y W T L A F I T K T I K F V | GI 1311534 |
| 125 | H N I E T S N F P K L L I A L L I Y W T L A F I T K T I K F V | GI 784874 |
| 156 | K F L D H A I G F S Q L R F C L T G L L V I L Y G M L L V E | SURH |
| 156 | K F L D H A I A F S Q V R F C L T G L L V I L Y G M L L V E | GI 1369844 |
| 156 | K F Y D H A I G F S Q L R F C L T G L L V I L Y G M L L V E | GI 1311534 |
| 156 | K F Y D H A I G F S Q L R F C L T G L L V I L Y G M L L V E | GI 784874 |
| 187 | V N V I R V R R Y I F F K T P R E V K P P E D L Q D L G V R F | SURH |
| 187 | V N V I R V R R Y I F F K T P R E V K P P E D L Q D L G V R F | GI 1369844 |
| 187 | V N V I R V R R Y V F F K T P R E V K P P E D L Q D L G V R F | GI 1311534 |
| 187 | V N V I R V R R Y I F F K T P R E V K P P E D L Q D L G V R F | GI 784874 |
| 218 | L Q P F V N L L S K G T Y W W M N A F I K T A H K K P X D L R | SURH |
| 218 | L Q P F V N L L S K G T Y W W M N A F I K T A H K K P I D L R | GI 1369844 |
| 218 | L Q P F V N L L S K G T Y W W M N A F I K T A H K K P I D L R | GI 1311534 |
| 218 | L Q P F V N L L S K G T Y W W M N A F I K T A H K K P I D L R | GI 784874 |
| 249 | A I G K L P I A M R A L T N Y Q R L C E A F D A Q - R K D I Q | SURH |
| 249 | A I G K L P I A M R A L T N Y Q R L C E A F D A Q V R K D I Q | GI 1369844 |
| 249 | A I G K L P I A M R A L T N Y Q R L C L A F D A Q A R K D T Q | GI 1311534 |
| 249 | A I A K L P I A M R A L T N Y Q R L C V A F D A Q A R K D T Q | GI 784874 |
| 279 | G T Q G A R A I W Q A L S H A F G R R L V L S S T F R I L A D | SURH |
| 280 | G T Q G A R A I W Q A L S H A F G R R L V L S S T F R I L A D | GI 1369844 |
| 280 | S Q Q G A R A I W R A L C H A F G R R L V L S S T F R I L A D | GI 1311534 |
| 280 | S P Q G A R A I W R A L C H A F G R R L I L S S T F R I L A D | GI 784874 |
| 310 | L L G F A G P L C I F G I V D H L G K E N D V F Q P K T Q F L | SURH |
| 311 | L L G F A G P L C I F G I V D H L G K E N D V F Q P K T Q F L | GI 1369844 |
| 311 | L L G F A G P L C I F G I V D H L G K E N H V F Q P K T Q F L | GI 1311534 |
| 311 | L L G F A G P L C I F G I V D H L G K E N H V F Q P K T Q F L | GI 784874 |
| 341 | G V Y F V S S Q E F L A N A Y V L A V L L F L A L L Q R T F | SURH |
| 342 | G V Y F V S S Q E F L A N A Y V L A V L L F L A L L Q R T F | GI 1369844 |
| 342 | G V Y F V S S Q E F L G N A Y V L A V L L F L A L L Q R T F | GI 1311534 |
| 342 | G V Y F V S S Q E F L G N A Y V L A V L L F L A L L Q R T F | GI 784874 |
| 372 | L Q A S Y Y V A I E T G I N L R G A I Q T K I Y N K I M H L S | SURH |
| 373 | L Q A S Y Y V A I E T G I N L R G A I Q T K I Y N K I M H L S | GI 1369844 |
| 373 | L Q A S Y Y V A I E T G I N L R G A I Q T K I Y N K I M H L S | GI 1311534 |
| 373 | L Q A S Y Y V A I E T G I N L R G A I Q T K I Y N K I M H M S | GI 784874 |

FIGURE 2A

| | | |
|---|---|---|
| 403 | T S N L S M G E M T A G Q I C N L V A I D T N Q L M W F F F L | SURH |
| 404 | T S N L S M G E M T A G Q I C N L V A I D T N Q L M W F F F L | GI 1369844 |
| 404 | T S N L S M G E M T A G Q I C N L V A I D T N Q L M W F F F L | GI 1311534 |
| 404 | T S N L S M G E M T A G Q I C N L V A I D T N Q L M W F F F L | GI 784874 |
| 434 | C P N L W A M P V Q I I V G V I L L Y Y I L G V S A L I G A A | SURH |
| 435 | C P N L W A M P V Q I I V G V I L L Y Y I L G V S A L I G A A | GI 1369844 |
| 435 | C P N L W A M P V Q I I V G V I L L Y Y I L G V S A L I G A A | GI 1311534 |
| 435 | C P N L W T M P V Q I I V G V I L L Y Y I L G V S A L I G A A | GI 784874 |
| 465 | V I I L L A P V Q Y F V A T K L S Q A Q R S T L E Y S N E R L | SURH |
| 466 | V I I L L A P V Q Y F V A T K L S Q A Q R T T L E Y S N E R L | GI 1369844 |
| 466 | V I I L L A P V Q Y F V A T K L S Q A Q R T T L E Y S N E R L | GI 1311534 |
| 466 | V I I L L A P V Q Y F V A T K L S Q A Q R T T L E H S N E R L | GI 784874 |
| 496 | K Q T N E M L R G I K L L K L Y A W E N I F R T R V E T T R R | SURH |
| 497 | K Q T N E M L R G I K L L K L Y A W E N I F R T R V E T T R R | GI 1369844 |
| 497 | K Q T N E M L R G I K L L K L Y A W E N I F C S R V E K T R R | GI 1311534 |
| 497 | K Q T N E M L R G M K L L K L Y A W E S I F C S R V E V T R R | GI 784874 |
| 527 | K E M T S L R A F A I Y T S I S I F M N T A I P I A A V L I T | SURH |
| 528 | K E M T S L R A F A I Y T S I S I F M N T A I P I A A V L I T | GI 1369844 |
| 528 | K E M T S L R A F A V Y T S I S I F M N T A I P I A A V L I T | GI 1311534 |
| 528 | K E M T S L R A F A V Y T S I S I F M N T A I P I A A V L I T | GI 784874 |
| 558 | F V G H V S F F K E A D F S P S V A F A S L S L F H I L V T P | SURH |
| 559 | F V G H V S F F K E A D F S P S V A F A S L S L F H I L V T P | GI 1369844 |
| 559 | F V G H V S F F K E S D F S P S V A F A S L S L F H I L V T P | GI 1311534 |
| 559 | F V G H V S F F K E S D L S P S V A F A S L S L F H I L V T P | GI 784874 |
| 589 | L F L L S S V V R S T V K A L V S V Q K L S E F L S S A E I R | SURH |
| 590 | L F L L S S V V R S T V K A L V S V Q K L S E F L S S A E I R | GI 1369844 |
| 590 | L F L L S S V V R S T V K A L V S V Q K L S E F L S S A E I R | GI 1311534 |
| 590 | L F L L S S V V R S T V K A L V S V Q K L S E F L S S A E I R | GI 784874 |
| 620 | E E Q C A P H E P T P Q G P A S K Y Q A V P L R V V N K R P | SURH |
| 621 | E E Q C A P H E P T P Q G P A S K Y Q A V P L R V V N K R P | GI 1369844 |
| 621 | E E Q C A P R E P A P Q G Q A G K Y Q A V P L K V V N K R P | GI 1311534 |
| 621 | E E Q C A P R E P A P Q G Q A G K Y Q A V P L K V V N K R P | GI 784874 |
| 651 | A R E D C R G L T G P L Q S L V P S A D G D A D N C C V Q I M | SURH |
| 652 | A R E D C R G L T G P L Q S L V P S A D G D A D N C C V Q I M | GI 1369844 |
| 652 | A R E V R D L L G P L Q R L T P S T D G D A D N F C V Q I I | GI 1311534 |
| 652 | A R E V R D L L G P L Q R L A P S M D G D A D N F C V Q I I | GI 784874 |
| 682 | G G Y F T W T P D G I P T L S N I T I R I P R G Q L T M I V G | SURH |
| 683 | G G Y F T W T P D G I P T L S N I T I R I P R G Q L T M I V G | GI 1369844 |
| 683 | G G F F T W T P D G I P T L S N I T I R I P R G Q L T M I V G | GI 1311534 |
| 683 | G G F F T W T P D G I P T L S N I T I R I P R G Q L T M I V G | GI 784874 |
| 713 | Q V G C G K S S L L L A A L G E M Q K V S G A V F W S S S L P | SURH |
| 714 | Q V G C G K S S L L L A A L G E M Q K V S G A V F W S S - L P | GI 1369844 |
| 714 | Q V G C G K S S L L L A T L G E M Q K V S G A V F W N S - L P | GI 1311534 |
| 714 | Q V G C G K S S L L L A T L G E M Q K V S G A V F W N S N L P | GI 784874 |
| 744 | D S E I G E D P S P E R E T A T D L D I R K R G P V A Y A S Q | SURH |
| 744 | D S E I G E D P S P E R E T A T D L D I R K R G P V A Y A S Q | GI 1369844 |
| 744 | D S E G E D P S N P E R E T A D S D A R S R G P V A Y A S Q | GI 1311534 |
| 745 | D S E G R G P Q Q P R A G D S S W L G Y Q E Q R P R G Y A S Q | GI 784874 |
| 775 | K P W L L N A T V E E N I I F E S P F N K Q R Y K M V I E A C | SURH |
| 775 | K P W L L N A T V E E N I I F E S P F N K Q R Y K M V I E A C | GI 1369844 |
| 775 | K P W L L N A T V E E N I T F E S P F N K Q R Y K M V I E A C | GI 1311534 |
| 776 | K P W L L N A T V E E N I T F E S P F N P Q R Y K M V I E A C | GI 784874 |

FIGURE 2B

```
806  S L Q P D I D I L P H G D Q T Q I G E R G I N L S G G Q R Q R   SURH
806  S L Q P D I D I L P H G D Q T Q I G E R G I N L S G G Q R Q R   GI 1369844
806  S L Q P D I D I L P H G D Q T Q I G E R G I N L S G G Q R P G   GI 1311534
807  S L Q P D I D I L P H G D Q T Q I G E R G I N L S G G Q R P D   GI 784874

837  I S V A R A L Y Q H A N V V F L D D P F S A L D I H L S D H L   SURH
837  I S V A R A L Y Q H A N V V F L D D P F S A L D I H L S D H L   GI 1369844
837  I S V A R A L Y Q H T N V V F L D D P F S A L D V H L S D H L   GI 1311534
838  Q C G P E P S T S R P M F V F L D D P F S A L D V H L S D H L   GI 784874

868  M Q A G I L E L L R D D K R T V V L V T H K L Q Y L P H A D W   SURH
868  M Q A G I L E L L R D D K R T V V L V T H K L Q Y L P H A D W   GI 1369844
868  M Q A G I L E L L R D D K R T V V L V T H K L Q Y L P H A D W   GI 1311534
869  M Q A G I L E L L R D D K R T V V L V T H K L Q Y L P H A D W   GI 784874

899  I I A M K D G T I Q R E G T S R T S R G L N A S S L S T G R P   SURH
899  I I A M K D G T I Q R E G T L K D F Q R - S E C Q L F E H W K   GI 1369844
899  I I A M K D G T I Q R E G T L K D F Q R - S E C Q L F E H W K   GI 1311534
900  I I A M K D G T I Q R E G T L K D F Q R - S E C Q L F E H W K   GI 784874

930  H - - E P T G P R A G E G N V T E R K A T E P P R A Y L V P C   SURH
929  T L M N R D Q E L E K E T V T E R K A T E P P Q G L S R A M   GI 1369844
929  T L M N R D Q E L E K E T V M E R K A P E P S Q G L P R A M   GI 1311534
930  T L M N R D Q E L E K E T V M E R K A S E P S Q G L P R A M   GI 784874

959  P R R D G L L Q D E E E E E E A A E N E E D D Y L S S M L H   SURH
960  S S R D G L L Q D E E E E E E A A E S E E D D N L S S M L H   GI 1369844
960  S S R D G L L L D E D E E E E E A A E S E E D D N L S S V L H   GI 1311534
961  S S R D G L L L D E E E E E E A A E S E E D D N L S S V L H   GI 784874

990  Q R A E I P W R A C X K Y L S S A G I L L L S L L V F S Q L L   SURH
991  Q R A E I P W R A C A K Y L S S A G I L L L S L L V F S Q L L   GI 1369844
991  Q R A K I P W R A C T K Y L S S A G I L L L S L L V F S Q L L   GI 1311534
992  Q R A K I P W R A C T K Y L S S A G I L L L S L L V F S Q L L   GI 784874

1021 K H M V L V A I D Y W L A K W T D S A L T L T P A T R N C S L   SURH
1022 K H M V L V A I D Y W L A K W T D S A L T L T P A A R N C S L   GI 1369844
1022 K H M V L V A I D Y W L A K W T D S A L V L S P A A R N C S L   GI 1311534
1023 K H M V L V A I D Y W L A K W T D S A L V L S P A A R N C S L   GI 784874

1052 N Q E C T L N Q T V Y A L V F T V L C S L G I V L C L V T S V   SURH
1053 S Q E C T L D Q T V Y A M V F T A V C S L G I V L C L V T S V   GI 1369844
1053 S Q E C A L D Q S V Y A M V F T V L C S L G I A L C L V T S V   GI 1311534
1054 S Q E C D L D Q S V Y A M V F T L L C S L G I V L C L V T S V   GI 784874

1083 T V E W T G L K V A K R L H R S L L N R I I L A P M R F F E T   SURH
1084 T V E W T G L K V A K R L H R S L L N R I I L A P M R F F E T   GI 1369844
1084 T V E W T G L K V A K R L H R S L L N R I I L A P M R F F E T   GI 1311534
1085 T V E W T G L K V A K R L H R S L L N R I I L A P M R F F E T   GI 784874

1114 T P L G S I L N R F S S D C N T I D Q H I P S T L E C L S R S   SURH
1115 T P L G S I L N R F S S D C N T I D Q H I P S T L E C L S R S   GI 1369844
1115 T P L G S I L N R F S S D C N T I D Q H I P S T L E C L S R S   GI 1311534
1116 T P L G S I L N R F S S D C N T I D Q H I P S T L E C L S R S   GI 784874

1145 T L L C V S A L A V I S Y V T P V F L V A L L P L A I V C Y F   SURH
1146 T L L C V S A L A V I S Y V T P V F L V A L L P L A I V C Y F   GI 1369844
1146 T L L C V S A L A V I S Y V T P V F L V A L L P L A V V C Y F   GI 1311534
1147 T L L C V S A L T V I S Y V T P V F L V A L L P L A V V C Y F   GI 784874

1176 I Q K Y F R V A S R D L Q Q L D D T T Q L P L L S H F A E T V   SURH
1177 I Q K Y F R V A S R D L Q Q L D D T T Q L P L L S H F A E T V   GI 1369844
1177 I Q K Y F R V A S R D L Q Q L D D T T Q L P L L S H F A E T V   GI 1311534
1178 I Q K Y F R V A S R D L Q Q L D D T T Q L P L V S H F A E T V   GI 784874
```

FIGURE 2C

```
1207  E G L T T I R A F R Y E A R F Q Q K L L E Y T D S N N I A S L   SURH
1208  E G L T T I R A F R Y E A R F Q Q K L L E Y T D S N N I A S L   GI 1369844
1208  E G L T T I R A F R Y E A R F Q Q K L L E Y T D S N N I A S L   GI 1311534
1209  E G L T T I R A F R Y E A R F Q Q K L L E Y T D S N N I A S L   GI 784874

1238  F L T A A N R W L E V R M E Y I G A C V V L I A A V T S I S N   SURH
1239  F L T A A N R W L E V R M E Y I G A C V V L I A A V T S I S N   GI 1369844
1239  F L T A A N R W L E V R M E Y I G A C V V L I A A A T S I S N   GI 1311534
1240  F L T A A N R W L E V C M E Y I G A C V V L I A A A T S I S N   GI 784874

1269  S L H R E L S A G L V G L G L T Y A L M V S N Y L N W M V R N   SURH
1270  S L H R E L S A G L V G L G L T Y A L M V S N Y L N W M V R N   GI 1369844
1270  S L H R E L S A G L V G L G L T Y A L M V S N Y L N W M V R N   GI 1311534
1271  S L H R E L S A G L V G L G L T Y A L M V S N Y L N W M V R N   GI 784874

1300  L A D M E L Q L G A V K R I H G L L K T E A E S Y E G L L A P   SURH
1301  L A D M E L Q L G A V K R I H G L L K T E A E S Y E G L L A P   GI 1369844
1301  L A D M E I Q L G A V K G I H T L L K T E A E S Y E G L L A P   GI 1311534
1302  L A D M E I Q L G A V K R I H A L L K T E A E S Y E G L L A P   GI 784874

1331  S L I P K N W P D Q G K I Q I Q N L S V R Y D S S L K P V L K   SURH
1332  S L I P K N W P D Q G K I Q I Q N L S V R Y D S S L K P V L K   GI 1369844
1332  S L I P K N W P D Q G K I Q I Q N L S V R Y D S S L K P V L K   GI 1311534
1333  S L I P K N W P D Q G K I Q I Q N L S V R Y D S S L K P V L K   GI 784874

1362  H V N A L I S P G Q K I G I C G R T G S G K S S F S L A F F R   SURH
1363  H V N A L I S P G Q K I G I C G R T G S G K S S F S L A F F R   GI 1369844
1363  H V N A L I S P G Q K I G I C G R T G S G K S S F S L A F F R   GI 1311534
1364  H V N T L I S P G Q K I G I C G R T G S G K S S F S L A F F R   GI 784874

1393  M V D T F E G H I I I D G I D I A K L P L H T L R S R L S I I   SURH
1394  M V D T F E G H I I I D G I D I A K L P L H T L R S R L S I I   GI 1369844
1394  M V D M F E G R I I I D G I D I A K L P L H T L R S R L S I I   GI 1311534
1395  M V D M F E G R I I I D G I D I A K L P L H T L R S R L S I I   GI 784874

1424  L Q D P V L F S G T I R F N L D P E R K C S D S T L W E A L E   SURH
1425  L Q D P V L F S G T I R F N L D P E R K C S D S T L W E A L E   GI 1369844
1425  L Q D P V L F S G T I R F N L D P E K K C S D S T L W E A L E   GI 1311534
1426  L Q D P V L F S G T I R F N L D P E K K C S D S T L W E A L E   GI 784874

1455  I A Q L K L V V K A L P G G L D A I I T E G G E N F S Q G Q R   SURH
1456  I A Q L K L V V K A L P G G L D A I I T E G G E N F S Q G Q R   GI 1369844
1456  I A Q L K L V V K A L P G G L D A I I T E G G E N F S Q G Q R   GI 1311534
1457  I A Q L K L V V K A L P G G L D A I I T E G G E N F S Q G Q R   GI 784874

1486  Q L F C L A R A F V R K T S I F I M D E A T A S I D M A T E N   SURH
1487  Q L F C L A R A F V R K T S I F I M D E A T A S I D M A T E N   GI 1369844
1487  Q L F C L A R A F V R K T S I F I M D E A T A S I D M A T E N   GI 1311534
1488  Q L F C L A R A F V R K T S I F I M D E A T A S I D M A T E N   GI 784874

1517  I L Q K V V M T A F A D R T V V T I A H R V H T I L S A D L V   SURH
1518  I L Q K V V M T A F A D R T V V T I A H R V H T I L S A D L V   GI 1369844
1518  I L Q K V V M T A F A D R T V V T I A H R V H T I L S A D L V   GI 1311534
1519  I L Q K V V M T A F A D R T V V T I A H R V H T I L S A D L V   GI 784874

1548  I V L K R G A I L E F D K P E K L L S R K D S V F A S F V R A   SURH
1549  I V L K R G A I L E F D K P E K L L S R K D S V F A S F V R A   GI 1369844
1549  M V L K R G A I L E F D K P E K L L S Q K D S V F A S F V R A   GI 1311534
1550  M V L K R G A I L E F D K P E T L L S Q K D S V F A S F V R A   GI 784874

1579  D K   SURH
1580  D K   GI 1369844
1580  D K   GI 1311534
1581  D K   GI 784874
```

FIGURE 2D

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 1580 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY:
      (B) CLONE: Consensus (xi) SEQUENCE DESCRIPTION: SEQ ID NO:1:

```
Met Pro Leu Ala Phe Cys Gly Ser Glu Asn His Ser Ala Ala Tyr Arg
 1               5                  10                  15

Val Asp Gln Gly Val Leu Asn Asn Gly Cys Phe Val Asp Ala Leu Asn
            20                  25                  30
```

-continued

```
Val Val Pro His Val Phe Leu Leu Phe Ile Thr Phe Pro Ile Leu Phe
         35                  40                  45

Ile Gly Trp Gly Ser Gln Ser Ser Lys Val His Ile His His Ser Thr
 50                  55                  60

Trp Leu His Phe Pro Gly His Asn Leu Arg Trp Ile Leu Thr Phe Met
 65              70                  75                      80

Leu Leu Phe Val Leu Val Cys Glu Ile Ala Glu Gly Ile Leu Ser Asp
                 85                  90                  95

Gly Val Thr Glu Ser His His Leu His Leu Tyr Met Pro Ala Gly Met
             100                 105                 110

Ala Phe Met Ala Ala Val Thr Ser Val Val Tyr Tyr His Asn Ile Glu
             115                 120                 125

Thr Ser Asn Phe Pro Lys Leu Leu Ile Ala Leu Leu Val Tyr Trp Thr
130                 135                 140

Leu Ala Phe Ile Thr Lys Thr Ile Lys Phe Val Lys Phe Leu Asp His
145                 150                 155                 160

Ala Ile Gly Phe Ser Gln Leu Arg Phe Cys Leu Thr Gly Leu Leu Val
                 165                 170                 175

Ile Leu Tyr Gly Met Leu Leu Val Glu Val Asn Val Ile Arg Val
             180                 185                 190

Arg Arg Tyr Ile Phe Phe Lys Thr Pro Arg Glu Val Lys Pro Pro Glu
             195                 200                 205

Asp Leu Gln Asp Leu Gly Val Arg Phe Leu Gln Pro Phe Val Asn Leu
             210                 215                 220

Leu Ser Lys Gly Thr Tyr Trp Trp Met Asn Ala Phe Ile Lys Thr Ala
225                 230                 235                 240

His Lys Lys Pro Xaa Asp Leu Arg Ala Ile Gly Lys Leu Pro Ile Ala
                 245                 250                 255

Met Arg Ala Leu Thr Asn Tyr Gln Arg Leu Cys Glu Ala Phe Asp Ala
             260                 265                 270

Gln Arg Lys Asp Ile Gln Gly Thr Gln Gly Ala Arg Ala Ile Trp Gln
             275                 280                 285

Ala Leu Ser His Ala Phe Gly Arg Arg Leu Val Leu Ser Ser Thr Phe
290                 295                 300

Arg Ile Leu Ala Asp Leu Leu Gly Phe Ala Gly Pro Leu Cys Ile Phe
305                 310                 315                 320

Gly Ile Val Asp His Leu Gly Lys Glu Asn Asp Val Phe Gln Pro Lys
                 325                 330                 335

Thr Gln Phe Leu Gly Val Tyr Phe Val Ser Ser Gln Glu Phe Leu Ala
             340                 345                 350

Asn Ala Tyr Val Leu Ala Val Leu Leu Phe Leu Ala Leu Leu Leu Gln
             355                 360                 365

Arg Thr Phe Leu Gln Ala Ser Tyr Tyr Val Ala Ile Glu Thr Gly Ile
             370                 375                 380

Asn Leu Arg Gly Ala Ile Gln Thr Lys Ile Tyr Asn Lys Ile Met His
385                 390                 395                 400

Leu Ser Thr Ser Asn Leu Ser Met Gly Glu Met Thr Ala Gly Gln Ile
                 405                 410                 415

Cys Asn Leu Val Ala Ile Asp Thr Asn Gln Leu Met Trp Phe Phe Phe
                 420                 425                 430

Leu Cys Pro Asn Leu Trp Ala Met Pro Val Gln Ile Ile Val Gly Val
             435                 440                 445
```

```
Ile Leu Leu Tyr Tyr Ile Leu Gly Val Ser Ala Leu Ile Gly Ala Ala
    450                 455                 460

Val Ile Ile Leu Leu Ala Pro Val Gln Tyr Phe Val Ala Thr Lys Leu
465                 470                 475                 480

Ser Gln Ala Gln Arg Ser Thr Leu Glu Tyr Ser Asn Glu Arg Leu Lys
                485                 490                 495

Gln Thr Asn Glu Met Leu Arg Gly Ile Lys Leu Leu Lys Leu Tyr Ala
                500                 505                 510

Trp Glu Asn Ile Phe Arg Thr Arg Val Glu Thr Thr Arg Arg Lys Glu
                515                 520                 525

Met Thr Ser Leu Arg Ala Phe Ala Ile Tyr Thr Ser Ile Ser Ile Phe
    530                 535                 540

Met Asn Thr Ala Ile Pro Ile Ala Ala Val Leu Ile Thr Phe Val Gly
545                 550                 555                 560

His Val Ser Phe Phe Lys Glu Ala Asp Phe Ser Pro Ser Val Ala Phe
                565                 570                 575

Ala Ser Leu Ser Leu Phe His Ile Leu Val Thr Pro Leu Phe Leu Leu
                580                 585                 590

Ser Ser Val Val Arg Ser Thr Val Lys Ala Leu Val Ser Val Gln Lys
                595                 600                 605

Leu Ser Glu Phe Leu Ser Ser Ala Glu Ile Arg Glu Glu Gln Cys Ala
    610                 615                 620

Pro His Glu Pro Thr Pro Gln Gly Pro Ala Ser Lys Tyr Gln Ala Val
625                 630                 635                 640

Pro Leu Arg Val Val Asn Arg Lys Arg Pro Ala Arg Glu Asp Cys Arg
                645                 650                 655

Gly Leu Thr Gly Pro Leu Gln Ser Leu Val Pro Ser Ala Asp Gly Asp
                660                 665                 670

Ala Asp Asn Cys Cys Val Gln Ile Met Gly Gly Tyr Phe Thr Trp Thr
                675                 680                 685

Pro Asp Gly Ile Pro Thr Leu Ser Asn Ile Thr Ile Arg Ile Pro Arg
    690                 695                 700

Gly Gln Leu Thr Met Ile Val Gly Gln Val Gly Cys Gly Lys Ser Ser
705                 710                 715                 720

Leu Leu Leu Ala Ala Leu Gly Glu Met Gln Lys Val Ser Gly Ala Val
                725                 730                 735

Phe Trp Ser Ser Ser Leu Pro Asp Ser Glu Ile Gly Glu Asp Pro Ser
                740                 745                 750

Pro Glu Arg Glu Thr Ala Thr Asp Leu Asp Ile Arg Lys Arg Gly Pro
                755                 760                 765

Val Ala Tyr Ala Ser Gln Lys Pro Trp Leu Leu Asn Ala Thr Val Glu
    770                 775                 780

Glu Asn Ile Ile Phe Glu Ser Pro Phe Asn Lys Gln Arg Tyr Lys Met
785                 790                 795                 800

Val Ile Glu Ala Cys Ser Leu Gln Pro Asp Ile Asp Ile Leu Pro His
                805                 810                 815

Gly Asp Gln Thr Gln Ile Gly Glu Arg Gly Ile Asn Leu Ser Gly Gly
                820                 825                 830

Gln Arg Gln Arg Ile Ser Val Ala Arg Ala Leu Tyr Gln His Ala Asn
                835                 840                 845

Val Val Phe Leu Asp Asp Pro Phe Ser Ala Leu Asp Ile His Leu Ser
    850                 855                 860

Asp His Leu Met Gln Ala Gly Ile Leu Glu Leu Leu Arg Asp Asp Lys
```

-continued

```
865                 870                 875                 880
Arg Thr Val Leu Val Thr His Lys Leu Gln Tyr Leu Pro His Ala
                885                 890                 895
Asp Trp Ile Ile Ala Met Lys Asp Gly Thr Ile Gln Arg Glu Gly Thr
            900                 905                 910
Ser Arg Thr Ser Arg Gly Leu Asn Ala Ser Ser Leu Ser Thr Gly Arg
            915                 920                 925
Pro His Glu Pro Thr Gly Pro Arg Ala Gly Glu Gly Asn Val Thr Glu
        930                 935                 940
Arg Lys Ala Thr Glu Pro Pro Arg Ala Tyr Leu Val Pro Cys Pro Arg
945                 950                 955                 960
Arg Asp Gly Leu Leu Gln Asp Glu Glu Glu Glu Glu Glu Ala Ala
                965                 970                 975
Glu Asn Glu Glu Asp Asp Tyr Leu Ser Ser Met Leu His Gln Arg Ala
                980                 985                 990
Glu Ile Pro Trp Arg Ala Cys Xaa Lys Tyr Leu Ser Ser Ala Gly Ile
            995                 1000                1005
Leu Leu Leu Ser Leu Leu Val Phe Ser Gln Leu Leu Lys His Met Val
    1010                1015                1020
Leu Val Ala Ile Asp Tyr Trp Leu Ala Lys Trp Thr Asp Ser Ala Leu
025                 1030                1035                1040
Thr Leu Thr Pro Ala Thr Arg Asn Cys Ser Leu Asn Gln Glu Cys Thr
                1045                1050                1055
Leu Asn Gln Thr Val Tyr Ala Leu Val Phe Thr Val Leu Cys Ser Leu
            1060                1065                1070
Gly Ile Val Leu Cys Leu Val Thr Ser Val Thr Val Glu Trp Thr Gly
        1075                1080                1085
Leu Lys Val Ala Lys Arg Leu His Arg Ser Leu Leu Asn Arg Ile Ile
    1090                1095                1100
Leu Ala Pro Met Arg Phe Phe Glu Thr Thr Pro Leu Gly Ser Ile Leu
105                 1110                1115                1120
Asn Arg Phe Ser Ser Asp Cys Asn Thr Ile Asp Gln His Ile Pro Ser
                1125                1130                1135
Thr Leu Glu Cys Leu Ser Arg Ser Thr Leu Leu Cys Val Ser Ala Leu
            1140                1145                1150
Ala Val Ile Ser Tyr Val Thr Pro Val Phe Leu Val Ala Leu Leu Pro
        1155                1160                1165
Leu Ala Ile Val Cys Tyr Phe Ile Gln Lys Tyr Phe Arg Val Ala Ser
    1170                1175                1180
Arg Asp Leu Gln Gln Leu Asp Asp Thr Thr Gln Leu Pro Leu Leu Ser
185                 1190                1195                1200
His Phe Ala Glu Thr Val Glu Gly Leu Thr Thr Ile Arg Ala Phe Arg
                1205                1210                1215
Tyr Glu Ala Arg Phe Gln Gln Lys Leu Leu Glu Tyr Thr Asp Ser Asn
            1220                1225                1230
Asn Ile Ala Ser Leu Phe Leu Thr Ala Ala Asn Arg Trp Leu Glu Val
        1235                1240                1245
Arg Met Glu Tyr Ile Gly Ala Cys Val Val Leu Ile Ala Ala Val Thr
    1250                1255                1260
Ser Ile Ser Asn Ser Leu His Arg Glu Leu Ser Ala Gly Leu Val Gly
265                 1270                1275                1280
Leu Gly Leu Thr Tyr Ala Leu Met Val Ser Asn Tyr Leu Asn Trp Met
                1285                1290                1295
```

```
Val Arg Asn Leu Ala Asp Met Glu Leu Gln Leu Gly Ala Val Lys Arg
        1300                1305                1310

Ile His Gly Leu Leu Lys Thr Glu Ala Glu Ser Tyr Glu Gly Leu Leu
    1315                1320                1325

Ala Pro Ser Leu Ile Pro Lys Asn Trp Pro Asp Gln Gly Lys Ile Gln
    1330                1335            1340

Ile Gln Asn Leu Ser Val Arg Tyr Asp Ser Ser Leu Lys Pro Val Leu
345             1350                1355                1360

Lys His Val Asn Ala Leu Ile Ser Pro Gly Gln Lys Ile Gly Ile Cys
        1365                1370                1375

Gly Arg Thr Gly Ser Gly Lys Ser Ser Phe Ser Leu Ala Phe Phe Arg
        1380                1385                1390

Met Val Asp Thr Phe Glu Gly His Ile Ile Ile Asp Gly Ile Asp Ile
        1395                1400                1405

Ala Lys Leu Pro Leu His Thr Leu Arg Ser Arg Leu Ser Ile Ile Leu
    1410                1415                1420

Gln Asp Pro Val Leu Phe Ser Gly Thr Ile Arg Phe Asn Leu Asp Pro
425             1430                1435                1440

Glu Arg Lys Cys Ser Asp Ser Thr Leu Trp Glu Ala Leu Glu Ile Ala
        1445                1450                1455

Gln Leu Lys Leu Val Val Lys Ala Leu Pro Gly Gly Leu Asp Ala Ile
        1460                1465                1470

Ile Thr Glu Gly Gly Glu Asn Phe Ser Gln Gly Gln Arg Gln Leu Phe
    1475                1480                1485

Cys Leu Ala Arg Ala Phe Val Arg Lys Thr Ser Ile Phe Ile Met Asp
    1490                1495                1500

Glu Ala Thr Ala Ser Ile Asp Met Ala Thr Glu Asn Ile Leu Gln Lys
505             1510                1515                1520

Val Val Met Thr Ala Phe Ala Asp Arg Thr Val Val Thr Ile Ala His
            1525                1530                1535

Arg Val His Thr Ile Leu Ser Ala Asp Leu Val Ile Val Leu Lys Arg
        1540                1545                1550

Gly Ala Ile Leu Glu Phe Asp Lys Pro Glu Lys Leu Leu Ser Arg Lys
        1555                1560                1565

Asp Ser Val Phe Ala Ser Phe Val Arg Ala Asp Lys
    1570                1575                1580

(2) INFORMATION FOR SEQ ID NO:2:

(i) SEQUENCE CHARACTERISTICS:
        (A) LENGTH: 4931 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE: Consensus (xi) SEQUENCE DESCRIPTION: SEQ ID NO:2:

GAATTCCCGG GTCGACCCAC GCGTCCGCCG CGCCCGCGCC GCCATGCCCC TGGCCTTCTG      60

CGGCAGCGAG AACCACTCGG CCGCCTACCG GGTGGACCAG GGGGTCCTCA ACAACGGCTG     120

CTTTGTGGAC GCGCTCAACG TGGTGCCGCA CGTCTTCCTA CTCTTCATCA CCTTCCCCAT     180

CCTCTTCATT GGATGGGGAA GTCAGAGCTC CAAGGTGCAC ATCCACCACA GCACATGGCT     240
```

-continued

```
TCATTTCCCT GGGCACAACC TGCGGTGGAT CCTGACCTTC ATGCTGCTCT TCGTCCTGGT    300
GTGTGAGATT GCAGAGGGCA TCCTGTCTGA TGGGGTGACC GAATCCCACC ATCTGCACCT    360
GTACATGCCA GCCGGGATGG CGTTCATGGC TGCTGTCACC TCCGTGGTCT ACTATCACAA    420
CATCGAGACT TCCAACTTCC CCAAGCTGCT AATTGCCCTG CTGGTGTATT GGACCCTGGC    480
CTTCATCACC AAGACCATCA AGTTTGTCAA GTTCTTGGAC CACGCCATCG GCTTCTCGCA    540
GCTACGCTTC TGCCTCACAG GGCTGCTGGT GATCCTCTAT GGGATGCTGC TCCTCGTGGA    600
GGTCAATGTC ATCAGGGTGA GGAGATACAT CTTCTTCAAG ACACCGAGGG AGGTGAAGCC    660
TCCCGAGGAC CTGCAAGACC TGGGGGTACG CTTCCTGCAG CCCTTCGTGA ATCTGCTGTC    720
CAAAGGCACC TACTGGTGGA TGAACGCCTT CATCAAGACT GCCCACAAGA AGCCCRTCGA    780
CTTGCGAGCC ATCGGGAAGC TGCCCATCGC CATGAGGGCC CTCACCAACT ACCAACGGCT    840
CTGCGAGGCC TTTGACGCCC AGCGGAAGGA CATTCAGGGC ACTCAAGGTG CCCGGGCCAT    900
CTGGCAGGCA CTCAGCCATG CCTTCGGGAG GCGCCTGGTC CTCAGCAGCA CTTTCCGCAT    960
CTTGGCCGAC CTGCTGGGCT CGCCGGGCC ACTGTGCATC TTTGGGATCG TGGACCACCT   1020
TGGGAAGGAG AACGACGTCT CCAGCCCAA GACACAATTT CTCGGGGTTT ACTTTGTCTC   1080
ATCCCAAGAG TTCCTTGCCA ATGCCTACGT CTTAGCTGTG CTTCTGTTCC TTGCCCTCCT   1140
ACTGCAAAGG ACATTTCTGC AAGCATCCTA CTATGTGGCC ATTGAAACTG GAATTAACTT   1200
GAGAGGAGCA ATACAGACCA AGATTTACAA TAAAATTATG CACCTGTCCA CCTCCAACCT   1260
GTCCATGGGA GAAATGACTG CTGGACAGAT CTGYAATCTG GTTGCCATCG ACACCAATCA   1320
GCTCATGTGG TTTTTCTTCT TGTGCCCAAA CCTCTGGGCT ATGCCAGTAC AGATCATTGT   1380
GGGTGTGATT CTCCTCTACT ACATACTCGG AGTCAGTGCC TTAATTGGAG CAGCTGTCAT   1440
CATTCTACTG GCTCCTGTCC AGTACTTCGT GGCCACCAAG CTGTCTCAGG CCCAGCGGAG   1500
CACACTGGAG TATTCCAATG AGCGGCTGAA GCAGACCAAC GAGATGCTCC GCGGCATCAA   1560
GCTGCTGAAG CTGTACGCCT GGGAGAACAT CTTCCGCACG CGGGTGGAGA CGACCCGCAG   1620
GAAGGAGATG ACCAGCCTCA GGGCCTTTGC CATCTATACC TCCATCTCCA TTTTCATGAA   1680
CACGGCCATC CCCATTGCAG CTGTCCTCAT AACTTTCGTG GGCCATGTCA GCTTCTTCAA   1740
AGAGGCCGAC TTCTCGCCCT CCGTGGCCTT TGCCTCCCTC TCCCTCTTCC ATATCTTGGT   1800
CACACCGCTG TTCCTGCTGT CCAGTGTGGT CCGATCTACC GTCAAAGCTC TAGTGAGCGT   1860
GCAAAAGCTA AGCGAGTTCC TGTCCAGTGC AGAGATCCGT GAGGAGCAGT GTGCCCCCCA   1920
TGAGCCCACA CCTCAGGGCC CAGCCAGCAA GTACCAGGCG GTGCCCCTCA GGGTTGTGAA   1980
CCGCAAGCGT CCAGCCCGGG AGGATTGTCG GGGCCTCACC GGCCCACTGC AGAGCCTGGT   2040
CCCCAGTGCA GATGGCGATG CTGACAACTG CTGTGTCCAG ATCATGGGAG GCTACTTCAC   2100
GTGGACCCCA GATGGAATCC CCACACTGTC CAACATCACC ATTCGTATCC CCCGAGGCCA   2160
GCTGACTATG ATCGTGGGGC AGGTGGGCTG CGGCAAGTCC TCGCTCCTTC TAGCCGCACT   2220
GGGGGAGATG CAGAAGGTCT CAGGGGCTGT CTTCTGGAGC AGCAGCCTTC CTGACAGCGA   2280
GATAGGAGAG GACCCCAGCC CAGAGCGGGA GACAGCGACC GACTTGGATA TCAGGAAGAG   2340
AGGCCCCGTG GCCTATGCTT CGCAGAAACC ATGGCTGCTA AATGCCACTG TGGAGGAGAA   2400
CATCATCTTT GAGAGTCCCT TCAACAAACA ACGGTACAAG ATGGTCATTG AAGCCTGCTC   2460
TCTGCAGCCA GACATCGACA TCCTGCCCCA TGGAGACCAG ACCCAGATTG GGAACGGGG   2520
CATCAACCTG TCTGGTGGTC AACGCCAGCG AATCAGTGTG GCCCGAGCCC TCTACCAGCA   2580
```

```
CGCCAACGTT GTCTTCTTGG ATGACCCCTT CTCAGCTCTG GATATCCATC TGAGTGACCA      2640

CTTAATGCAG GCCGGCATCC TTGAGCTGCT CCGGGACGAC AAGAGGACAG TGGTCTTAGT      2700

GACCCACAAG CTACAGTACC TGCCCCATGC AGACTGGATC ATTGCCATGA AGGATGGCAC      2760

CATCCAGAGG GAGGGTACCT CAAGGACTTC CAGAGGTCTG AATGCCAGCT CTTTGAGCAC      2820

TGGAAGACCT CATGAACCGA CAGGACCAAG AGCTGGAGAA GGAAATGTCA CAGAGAGAAA      2880

AGCCACAGAG CCACCCAGGG CCTATCTCGT GCCATGTCCT CGAAGGGATG GCCTTCTGCA      2940

GGATGAGGAA GAGGAGGAAG AGGAGGCAGC TGAGAACGAG GAGGATGACT ACCTGTCGTC      3000

CATGCTGCAC CAGCGTGCTG AGATCCCATG GCGAGCCTGC NCCAAGTACC TGTCCTCCGC      3060

CGGCATCCTG CTCCTGTCGT TGCTGGTCTT CTCACAGCTG CTCAAGCACA TGGTCCTGGT      3120

GGCCATCGAC TACTGGCTGG CCAAGTGGAC CGACAGCGCC CTGACCCTGA CCCCTGCAAC      3180

CAGGAACTGC TCCCTCAACC AGGAGTGCAC CCTCAACCAG ACTGTCTATG CCTTGGTGTT      3240

CACGGTGCTC TGCAGCCTGG GCATTGTGCT GTGCCTCGTC ACGTCTGTCA CTGTGGAGTG      3300

GACAGGGCTG AAGGTGGCCA AGAGACTGCA CCGCAGCCTG CTAAACCGGA TCATCCTAGC      3360

CCCCATGAGG TTTTTTGAGA CCACGCCCCT TGGGAGCATC CTGAACAGAT TTTCATCTGA      3420

CTGTAACACC ATCGACCAGC ACATCCCATC CACGCTGGAG TGCCTGAGCC GCTCCACCCT      3480

GCTCTGTGTC TCAGCCCTGG CCGTCATCTC CTATGTCACA CCTGTGTTCC TCGTGGCCCT      3540

CTTGCCCCTG GCCATCGTGT GCTACTTCAT CCAGAAGTAC TTCCGGGTGG CGTCCAGGGA      3600

CCTGCAGCAG CTGGATGACA CCACCCAGCT TCCACTTCTC TCACACTTTG CCGAAACCGT      3660

AGAAGGACTC ACCACCATCC GGGCCTTCAG GTATGAGGCC CGGTTCCAGC AGAAGCTTCT      3720

CGAATACACA GACTCCAACA ACATTGCTTC CCTCTTCCTC ACAGCTGCCA ACAGATGGCT      3780

GGAAGTCCGA ATGGAGTACA TCGGTGCATG TGTGGTGCTC ATCGCAGCGG TGACCTCCAT      3840

CTCCAACTCC CTGCACAGAG AGCTCTCTGC TGGCCTGGTG GGCCTGGGCC TTACCTACGC      3900

CCTAATGGTC TCCAACTACC TCAACTGGAT GGTGAGGAAC CTGGCAGACA TGGAGCTCCA      3960

GCTGGGGGCT GTGAAGCGCA TCCATGGGCT CCTGAAAACC GAGGCAGAGA GCTACGAGGG      4020

GCTCCTGGCA CCATCGCTGA TCCCAAAGAA CTGGCCAGAC CAAGGGAAGA TCCAGATCCA      4080

GAACCTGAGC GTGCGCTACG ACAGCTCCCT GAAGCCGGTG CTGAAGCACG TCAATGCCCT      4140

CATCTCCCCT GGACAGAAGA TCGGGATCTG CGGCCGCACC GGCAGTGGGA AGTCCTCCTT      4200

CTCTCTTGCC TTCTTCCGCA TGGTGGACAC GTTCGAAGGG CACATCATCA TTGATGGCAT      4260

TGACATCGCC AAACTGCCGC TGCACACCCT GCGCTCACGC CTCTCCATCA TCCTGCAGGA      4320

CCCCGTCCTC TTCAGCGGCA CCATCCGATT TAACCTGGAC CCTGAGAGGA AGTGCTCAGA      4380

TAGCACACTG TGGGAGGCCC TGGAAATCGC CCAGCTGAAG CTGGTGGTGA AGGCACTGCC      4440

AGGAGGCCTC GATGCCATCA TCACAGAAGG CGGGGAGAAT TTCAGCCAGG ACAGAGGCA       4500

GCTGTTCTGC CTGGCCCGGG CCTTCGTGAG GAAGACCAGC ATCTTCATCA TGGACGAGGC      4560

CACGGCTTCC ATTGACATGG CCACGGAAAA CATCCTCCAA AAGGTGGTGA TGACAGCCTT      4620

CGCAGACCGC ACTGTGGTCA CCATCGCGCA TCGAGTGCAC ACCATCCTGA GTGCAGACCT      4680

GGTGATCGTC CTGAAGCGGG GTGCCATCCT TGAGTTCGAT AAGCCAGAGA AGCTGCTCAG      4740

CCGGAAGGAC AGCGTCTTCG CCTCCTTCGT CCGTGCAGAC AAGTGACCTG CCAGAGCCCA      4800

AGTGCCATCC CACATTCGGA CCCTGCCCAT ACCCCTGCCT GGGTTTTCTA ACTGTAAATC      4860

ACTTGTAAAT AAATAGATTT GATTATTAAA AAAAAAAAAA AAAAAAAAAA AAAAAAAAA       4920

AAAAAAAAAA A                                                          4931
```

(2) INFORMATION FOR SEQ ID NO:3:

(i) SEQUENCE CHARACTERISTICS:
        (A) LENGTH: 1581 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 1369844

(xi) SEQUENCE DESCRIPTION: SEQ ID NO:3:

```
Met Pro Leu Ala Phe Cys Gly Ser Glu Asn His Ser Ala Ala Tyr Arg
 1               5                  10                  15

Val Asp Gln Gly Val Leu Asn Asn Gly Cys Phe Val Asp Val Leu Asn
             20                  25                  30

Val Val Pro His Val Phe Leu Leu Phe Ile Thr Phe Pro Ile Leu Phe
             35                  40                  45

Ile Gly Trp Gly Ser Gln Ser Ser Lys Val His Ile His His Ser Thr
 50                  55                  60

Trp Leu His Phe Pro Gly His Asn Leu Arg Trp Ile Leu Thr Phe Met
 65                      70                  75                  80

Leu Leu Phe Val Leu Val Cys Glu Ile Ala Glu Gly Ile Leu Ser Asp
                 85                  90                  95

Gly Val Thr Glu Ser His His Leu His Leu Tyr Met Pro Ala Gly Met
                100                 105                 110

Ala Phe Met Ala Ala Val Thr Ser Val Val Tyr Tyr His Asn Ile Glu
            115                 120                 125

Thr Ser Asn Phe Pro Lys Leu Leu Ile Ala Leu Leu Val Tyr Trp Thr
            130                 135                 140

Leu Ala Phe Ile Thr Lys Thr Ile Lys Phe Val Lys Phe Leu Asp His
145                 150                 155                 160

Ala Ile Ala Phe Ser Gln Val Arg Phe Cys Leu Thr Gly Leu Leu Val
                165                 170                 175

Ile Leu Tyr Gly Met Leu Leu Val Glu Val Asn Val Ile Arg Val
                180                 185                 190

Arg Arg Tyr Ile Phe Phe Lys Thr Pro Arg Glu Val Lys Pro Pro Glu
                195                 200                 205

Asp Leu Gln Asp Leu Gly Val Arg Phe Leu Gln Pro Phe Val Asn Leu
            210                 215                 220

Leu Ser Lys Gly Thr Tyr Trp Trp Met Asn Ala Phe Ile Lys Thr Ala
225                 230                 235                 240

His Lys Lys Pro Ile Asp Leu Arg Ala Ile Gly Lys Leu Pro Ile Ala
                245                 250                 255

Met Arg Ala Leu Thr Asn Tyr Gln Arg Leu Cys Glu Ala Phe Asp Ala
                260                 265                 270

Gln Val Arg Lys Asp Ile Gln Gly Thr Gln Gly Ala Arg Ala Ile Trp
            275                 280                 285

Gln Ala Leu Ser His Ala Phe Gly Arg Arg Leu Val Leu Ser Ser Thr
            290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn Asp Val Phe Gln Pro
```

-continued

```
                325                 330                 335
Lys Thr Gln Phe Leu Gly Val Tyr Phe Val Ser Ser Gln Glu Phe Leu
                340                 345                 350

Ala Asn Ala Tyr Val Leu Ala Val Leu Leu Phe Leu Ala Leu Leu Leu
                355                 360                 365

Gln Arg Thr Phe Leu Gln Ala Ser Tyr Tyr Val Ala Ile Glu Thr Gly
                370                 375                 380

Ile Asn Leu Arg Gly Ala Ile Gln Thr Lys Ile Tyr Asn Lys Ile Met
385                 390                 395                 400

His Leu Ser Thr Ser Asn Leu Ser Met Gly Glu Met Thr Ala Gly Gln
                405                 410                 415

Ile Cys Asn Leu Val Ala Ile Asp Thr Asn Gln Leu Met Trp Phe Phe
                420                 425                 430

Phe Leu Cys Pro Asn Leu Trp Ala Met Pro Val Gln Ile Ile Val Gly
                435                 440                 445

Val Ile Leu Leu Tyr Tyr Ile Leu Gly Val Ser Ala Leu Ile Gly Ala
                450                 455                 460

Ala Val Ile Ile Leu Leu Ala Pro Val Gln Tyr Phe Val Ala Thr Lys
465                 470                 475                 480

Leu Ser Gln Ala Gln Arg Thr Thr Leu Glu Tyr Ser Asn Glu Arg Leu
                485                 490                 495

Lys Gln Thr Asn Glu Met Leu Arg Gly Ile Lys Leu Leu Lys Leu Tyr
                500                 505                 510

Ala Trp Glu Asn Ile Phe Arg Thr Arg Val Glu Thr Arg Arg Lys
                515                 520                 525

Glu Met Thr Ser Leu Arg Ala Phe Ala Ile Tyr Thr Ser Ile Ser Ile
                530                 535                 540

Phe Met Asn Thr Ala Ile Pro Ile Ala Ala Val Leu Ile Thr Phe Val
545                 550                 555                 560

Gly His Val Ser Phe Phe Lys Glu Ala Asp Phe Ser Pro Ser Val Ala
                565                 570                 575

Phe Ala Ser Leu Ser Leu Phe His Ile Leu Val Thr Pro Leu Phe Leu
                580                 585                 590

Leu Ser Ser Val Val Arg Ser Thr Val Lys Ala Leu Val Ser Val Gln
                595                 600                 605

Lys Leu Ser Glu Phe Leu Ser Ser Ala Glu Ile Arg Glu Glu Gln Cys
610                 615                 620

Ala Pro His Glu Pro Thr Pro Gln Gly Pro Ala Ser Lys Tyr Gln Ala
625                 630                 635                 640

Val Pro Leu Arg Val Val Asn Arg Lys Arg Pro Ala Arg Glu Asp Cys
                645                 650                 655

Arg Gly Leu Thr Gly Pro Leu Gln Ser Leu Val Pro Ser Ala Asp Gly
                660                 665                 670

Asp Ala Asp Asn Cys Cys Val Gln Ile Met Gly Gly Tyr Phe Thr Trp
                675                 680                 685

Thr Pro Asp Gly Ile Pro Thr Leu Ser Asn Ile Thr Ile Arg Ile Pro
                690                 695                 700

Arg Gly Gln Leu Thr Met Ile Val Gly Gln Val Gly Cys Gly Lys Ser
705                 710                 715                 720

Ser Leu Leu Leu Ala Ala Leu Gly Glu Met Gln Lys Val Ser Gly Ala
                725                 730                 735

Val Phe Trp Ser Ser Leu Pro Asp Ser Glu Ile Gly Glu Asp Pro Ser
                740                 745                 750
```

-continued

```
Pro Glu Arg Glu Thr Ala Thr Asp Leu Asp Ile Arg Lys Arg Gly Pro
    755                 760                 765

Val Ala Tyr Ala Ser Gln Lys Pro Trp Leu Leu Asn Ala Thr Val Glu
    770                 775                 780

Glu Asn Ile Ile Phe Glu Ser Pro Phe Asn Lys Gln Arg Tyr Lys Met
785                 790                 795                 800

Val Ile Glu Ala Cys Ser Leu Gln Pro Asp Ile Asp Ile Leu Pro His
                805                 810                 815

Gly Asp Gln Thr Gln Ile Gly Arg Gly Ile Asn Leu Ser Gly Gly
                820                 825                 830

Gln Arg Gln Arg Ile Ser Val Ala Arg Ala Leu Tyr Gln His Ala Asn
                835                 840                 845

Val Val Phe Leu Asp Asp Pro Phe Ser Ala Leu Asp Ile His Leu Ser
    850                 855                 860

Asp His Leu Met Gln Ala Gly Ile Leu Glu Leu Leu Arg Asp Asp Lys
865                 870                 875                 880

Arg Thr Val Val Leu Val Thr His Lys Leu Gln Tyr Leu Pro His Ala
                885                 890                 895

Asp Trp Ile Ile Ala Met Lys Asp Gly Thr Ile Gln Arg Glu Gly Thr
                900                 905                 910

Leu Lys Asp Phe Gln Arg Ser Glu Cys Gln Leu Phe Glu His Trp Lys
    915                 920                 925

Thr Leu Met Asn Arg Gln Asp Gln Glu Leu Glu Lys Glu Thr Val Thr
    930                 935                 940

Glu Arg Lys Ala Thr Glu Pro Pro Gln Gly Leu Ser Arg Ala Met Ser
945                 950                 955                 960

Ser Arg Asp Gly Leu Leu Gln Asp Glu Glu Glu Glu Glu Glu Ala
                965                 970                 975

Ala Glu Ser Glu Glu Asp Asp Asn Leu Ser Ser Met Leu His Gln Arg
                980                 985                 990

Ala Glu Ile Pro Trp Arg Ala Cys Ala Lys Tyr Leu Ser Ser Ala Gly
                995                1000                1005

Ile Leu Leu Leu Ser Leu Leu Val Phe Ser Gln Leu Leu Lys His Met
   1010                1015                1020

Val Leu Val Ala Ile Asp Tyr Trp Leu Ala Lys Trp Thr Asp Ser Ala
 025                1030                1035                1040

Leu Thr Leu Thr Pro Ala Ala Arg Asn Cys Ser Leu Ser Gln Glu Cys
                1045                1050                1055

Thr Leu Asp Gln Thr Val Tyr Ala Met Val Phe Thr Ala Val Cys Ser
                1060                1065                1070

Leu Gly Ile Val Leu Cys Leu Val Thr Ser Val Thr Val Glu Trp Thr
                1075                1080                1085

Gly Leu Lys Val Ala Lys Arg Leu His Arg Ser Leu Leu Asn Arg Ile
    1090                1095                1100

Ile Leu Ala Pro Met Arg Phe Phe Glu Thr Thr Pro Leu Gly Ser Ile
 105                1110                1115                1120

Leu Asn Arg Phe Ser Ser Asp Cys Asn Thr Ile Asp Gln His Ile Pro
                1125                1130                1135

Ser Thr Leu Glu Cys Leu Ser Arg Ser Thr Leu Leu Cys Val Ser Ala
                1140                1145                1150

Leu Ala Val Ile Ser Tyr Val Thr Pro Val Phe Leu Val Ala Leu Leu
                1155                1160                1165
```

```
Pro Leu Ala Ile Val Cys Tyr Phe Ile Gln Lys Tyr Phe Arg Val Ala
    1170                1175                1180

Ser Arg Asp Leu Gln Gln Leu Asp Asp Thr Thr Gln Leu Pro Leu Leu
185                 1190                1195                1200

Ser His Phe Ala Glu Thr Val Glu Gly Leu Thr Thr Ile Arg Ala Phe
                1205                1210                1215

Arg Tyr Glu Ala Arg Phe Gln Gln Lys Leu Leu Glu Tyr Thr Asp Ser
                1220                1225                1230

Asn Asn Ile Ala Ser Leu Phe Leu Thr Ala Ala Asn Arg Trp Leu Glu
                1235                1240                1245

Val Arg Met Glu Tyr Ile Gly Ala Cys Val Val Leu Ile Ala Ala Val
            1250                1255                1260

Thr Ser Ile Ser Asn Ser Leu His Arg Glu Leu Ser Ala Gly Leu Val
265                 1270                1275                1280

Gly Leu Gly Leu Thr Tyr Ala Leu Met Val Ser Asn Tyr Leu Asn Trp
                1285                1290                1295

Met Val Arg Asn Leu Ala Asp Met Glu Leu Gln Leu Gly Ala Val Lys
                1300                1305                1310

Arg Ile His Gly Leu Leu Lys Thr Glu Ala Glu Ser Tyr Glu Gly Leu
            1315                1320                1325

Leu Ala Pro Ser Leu Ile Pro Lys Asn Trp Pro Asp Gln Gly Lys Ile
    1330                1335                1340

Gln Ile Gln Asn Leu Ser Val Arg Tyr Asp Ser Ser Leu Lys Pro Val
345                 1350                1355                1360

Leu Lys His Val Asn Ala Leu Ile Ser Pro Gly Gln Lys Ile Gly Ile
                1365                1370                1375

Cys Gly Arg Thr Gly Ser Gly Lys Ser Ser Phe Ser Leu Ala Phe Phe
            1380                1385                1390

Arg Met Val Asp Thr Phe Glu Gly His Ile Ile Ile Asp Gly Ile Asp
            1395                1400                1405

Ile Ala Lys Leu Pro Leu His Thr Leu Arg Ser Arg Leu Ser Ile Ile
    1410                1415                1420

Leu Gln Asp Pro Val Leu Phe Ser Gly Thr Ile Arg Phe Asn Leu Asp
425                 1430                1435                1440

Pro Glu Arg Lys Cys Ser Asp Ser Thr Leu Trp Glu Ala Leu Glu Ile
            1445                1450                1455

Ala Gln Leu Lys Leu Val Val Lys Ala Leu Pro Gly Gly Leu Asp Ala
            1460                1465                1470

Ile Ile Thr Glu Gly Gly Glu Asn Phe Ser Gln Gly Gln Arg Gln Leu
        1475                1480                1485

Phe Cys Leu Ala Arg Ala Phe Val Arg Lys Thr Ser Ile Phe Ile Met
    1490                1495                1500

Asp Glu Ala Thr Ala Ser Ile Asp Met Ala Thr Glu Asn Ile Leu Gln
505                 1510                1515                1520

Lys Val Val Met Thr Ala Phe Ala Asp Arg Thr Val Val Thr Ile Ala
            1525                1530                1535

His Arg Val His Thr Ile Leu Ser Ala Asp Leu Val Ile Val Leu Lys
                1540                1545                1550

Arg Gly Ala Ile Leu Glu Phe Asp Lys Pro Glu Lys Leu Leu Ser Arg
        1555                1560                1565

Lys Asp Ser Val Phe Ala Ser Phe Val Arg Ala Asp Lys
    1570                1575                1580
```

(2) INFORMATION FOR SEQ ID NO:4:

(i) SEQUENCE CHARACTERISTICS:
        (A) LENGTH: 1581 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: Genbank
        (B) CLONE: 1311534

(xi) SEQUENCE DESCRIPTION: SEQ ID NO:4:

```
Met Pro Leu Ala Phe Cys Gly Thr Glu Asn His Ser Ala Ala Tyr Arg
 1               5                  10                  15

Val Asp Gln Gly Val Leu Asn Asn Gly Cys Phe Val Asp Ala Leu Asn
                20                  25                  30

Val Val Pro His Val Phe Leu Leu Phe Ile Thr Phe Pro Ile Leu Phe
            35                  40                  45

Ile Gly Trp Gly Ser Gln Ser Ser Lys Val His Ile His His Ser Thr
 50                  55                  60

Trp Leu His Phe Pro Gly His Asn Leu Arg Trp Ile Leu Thr Phe Ile
 65                  70                  75                  80

Leu Leu Phe Val Leu Val Cys Glu Ile Ala Glu Gly Ile Leu Ser Asp
                85                  90                  95

Gly Val Thr Glu Ser Arg His Leu His Leu Tyr Met Pro Ala Gly Met
            100                 105                 110

Ala Phe Met Ala Ala Ile Thr Ser Val Val Tyr Tyr His Asn Ile Glu
        115                 120                 125

Thr Ser Asn Phe Pro Lys Leu Leu Ile Ala Leu Leu Ile Tyr Trp Thr
130                 135                 140

Leu Ala Phe Ile Thr Lys Thr Ile Lys Phe Val Lys Phe Tyr Asp His
145                 150                 155                 160

Ala Ile Gly Phe Ser Gln Leu Arg Phe Cys Leu Thr Gly Leu Leu Val
                165                 170                 175

Ile Leu Tyr Gly Met Leu Leu Val Glu Val Asn Val Ile Arg Val
            180                 185                 190

Arg Arg Tyr Val Phe Phe Lys Thr Pro Arg Glu Val Lys Pro Pro Glu
        195                 200                 205

Asp Leu Gln Asp Leu Gly Val Arg Phe Leu Gln Pro Phe Val Asn Leu
    210                 215                 220

Leu Ser Lys Gly Thr Tyr Trp Trp Met Asn Ala Phe Ile Lys Thr Ala
225                 230                 235                 240

His Lys Lys Pro Ile Asp Leu Arg Ala Ile Gly Lys Leu Pro Ile Ala
                245                 250                 255

Met Arg Ala Leu Thr Asn Tyr Gln Arg Leu Cys Leu Ala Phe Asp Ala
            260                 265                 270

Gln Ala Arg Lys Asp Thr Gln Ser Gln Gln Gly Ala Arg Ala Ile Trp
        275                 280                 285

Arg Ala Leu Cys His Ala Phe Gly Arg Arg Leu Val Leu Ser Ser Thr
    290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn His Val Phe Gln Pro
                325                 330                 335
```

-continued

```
Lys Thr Gln Phe Leu Gly Val Tyr Phe Val Ser Ser Gln Glu Phe Leu
                340                 345                 350

Gly Asn Ala Tyr Val Leu Ala Val Leu Leu Phe Leu Ala Leu Leu Leu
            355                 360                 365

Gln Arg Thr Phe Leu Gln Ala Ser Tyr Tyr Val Ala Ile Glu Thr Gly
        370                 375                 380

Ile Asn Leu Arg Gly Ala Ile Gln Thr Lys Ile Tyr Asn Lys Ile Met
385                 390                 395                 400

His Leu Ser Thr Ser Asn Leu Ser Met Gly Glu Met Thr Ala Gly Gln
                405                 410                 415

Ile Cys Asn Leu Val Ala Ile Asp Thr Asn Gln Leu Met Trp Phe Phe
                420                 425                 430

Phe Leu Cys Pro Asn Leu Trp Ala Met Pro Val Gln Ile Ile Val Gly
            435                 440                 445

Val Ile Leu Leu Tyr Tyr Ile Leu Gly Val Ser Ala Leu Ile Gly Ala
        450                 455                 460

Ala Val Ile Ile Leu Leu Ala Pro Val Gln Tyr Phe Val Ala Thr Lys
465                 470                 475                 480

Leu Ser Gln Ala Gln Arg Thr Thr Leu Glu Tyr Ser Asn Glu Arg Leu
                485                 490                 495

Lys Gln Thr Asn Glu Met Leu Arg Gly Ile Lys Leu Leu Lys Leu Tyr
            500                 505                 510

Ala Trp Glu Asn Ile Phe Cys Ser Arg Val Glu Lys Thr Arg Arg Lys
        515                 520                 525

Glu Met Thr Ser Leu Arg Ala Phe Ala Val Tyr Thr Ser Ile Ser Ile
    530                 535                 540

Phe Met Asn Thr Ala Ile Pro Ile Ala Ala Val Leu Ile Thr Phe Val
545                 550                 555                 560

Gly His Val Ser Phe Lys Glu Ser Asp Phe Ser Pro Ser Val Ala
                565                 570                 575

Phe Ala Ser Leu Ser Leu Phe His Ile Leu Val Thr Pro Leu Phe Leu
                580                 585                 590

Leu Ser Ser Val Val Arg Ser Thr Val Lys Ala Leu Val Ser Val Gln
            595                 600                 605

Lys Leu Ser Glu Phe Leu Ser Ser Ala Glu Ile Arg Glu Glu Gln Cys
        610                 615                 620

Ala Pro Arg Glu Pro Ala Pro Gln Gly Gln Ala Gly Lys Tyr Gln Ala
625                 630                 635                 640

Val Pro Leu Lys Val Val Asn Arg Lys Arg Pro Ala Arg Glu Glu Val
                645                 650                 655

Arg Asp Leu Leu Gly Pro Leu Gln Arg Leu Thr Pro Ser Thr Asp Gly
                660                 665                 670

Asp Ala Asp Asn Phe Cys Val Gln Ile Ile Gly Phe Phe Thr Trp
            675                 680                 685

Thr Pro Asp Gly Ile Pro Thr Leu Ser Asn Ile Thr Ile Arg Ile Pro
        690                 695                 700

Arg Gly Gln Leu Thr Met Ile Val Gly Gln Val Gly Cys Gly Lys Ser
705                 710                 715                 720

Ser Leu Leu Leu Ala Thr Leu Gly Glu Met Gln Lys Val Ser Gly Ala
                725                 730                 735

Val Phe Trp Asn Ser Leu Pro Asp Ser Glu Gly Glu Asp Pro Ser Asn
            740                 745                 750

Pro Glu Arg Glu Thr Ala Ala Asp Ser Asp Ala Arg Ser Arg Gly Pro
```

-continued

```
            755                 760                 765
Val Ala Tyr Ala Ser Gln Lys Pro Trp Leu Leu Asn Ala Thr Val Glu
770                 775                 780

Glu Asn Ile Thr Phe Glu Ser Pro Phe Asn Lys Gln Arg Tyr Lys Met
785                 790                 795                 800

Val Ile Glu Ala Cys Ser Leu Gln Pro Asp Ile Asp Ile Leu Pro His
                805                 810                 815

Gly Asp Gln Thr Gln Ile Gly Glu Arg Gly Ile Asn Leu Ser Gly Gly
            820                 825                 830

Gln Arg Pro Gly Ile Ser Val Ala Arg Ala Leu Tyr Gln His Thr Asn
            835                 840                 845

Val Val Phe Leu Asp Asp Pro Phe Ser Ala Leu Asp Val His Leu Ser
            850                 855                 860

Asp His Leu Met Gln Ala Gly Ile Leu Glu Leu Leu Arg Asp Asp Lys
865                 870                 875                 880

Arg Thr Val Val Leu Val Thr His Lys Leu Gln Tyr Leu Pro His Ala
                885                 890                 895

Asp Trp Ile Ile Ala Met Lys Asp Gly Thr Ile Gln Arg Glu Gly Thr
            900                 905                 910

Leu Lys Asp Phe Gln Arg Ser Glu Cys Gln Leu Phe Glu His Trp Lys
            915                 920                 925

Thr Leu Met Asn Arg Gln Asp Gln Glu Leu Glu Lys Glu Thr Val Met
930                 935                 940

Glu Arg Lys Ala Pro Glu Pro Ser Gln Gly Leu Pro Arg Ala Met Ser
945                 950                 955                 960

Ser Arg Asp Gly Leu Leu Leu Asp Glu Asp Glu Glu Glu Glu Glu Ala
                965                 970                 975

Ala Glu Ser Glu Glu Asp Asp Asn Leu Ser Ser Val Leu His Gln Arg
            980                 985                 990

Ala Lys Ile Pro Trp Arg Ala Cys Thr Lys Tyr Leu Ser Ser Ala Gly
            995                 1000                1005

Ile Leu Leu Leu Ser Leu Leu Val Phe Ser Gln Leu Leu Lys His Met
    1010                1015                1020

Val Leu Val Ala Ile Asp Tyr Trp Leu Ala Lys Trp Thr Asp Ser Ala
025                 1030                1035                1040

Leu Val Leu Ser Pro Ala Ala Arg Asn Cys Ser Leu Ser Gln Glu Cys
                1045                1050                1055

Ala Leu Asp Gln Ser Val Tyr Ala Met Val Phe Thr Val Leu Cys Ser
                1060                1065                1070

Leu Gly Ile Ala Leu Cys Leu Val Thr Ser Val Thr Val Glu Trp Thr
            1075                1080                1085

Gly Leu Lys Val Ala Lys Arg Leu His Arg Ser Leu Leu Asn Arg Ile
    1090                1095                1100

Ile Leu Ala Pro Met Arg Phe Phe Glu Thr Thr Pro Leu Gly Ser Ile
105                 1110                1115                1120

Leu Asn Arg Phe Ser Ser Asp Cys Asn Thr Ile Asp Gln His Ile Pro
                1125                1130                1135

Ser Thr Leu Glu Cys Leu Ser Arg Ser Thr Leu Leu Cys Val Ser Ala
            1140                1145                1150

Leu Ala Val Ile Ser Tyr Val Thr Pro Val Phe Leu Val Ala Leu Leu
            1155                1160                1165

Pro Leu Ala Val Val Cys Tyr Phe Ile Gln Lys Tyr Phe Arg Val Ala
    1170                1175                1180
```

```
Ser Arg Asp Leu Gln Gln Leu Asp Asp Thr Thr Gln Leu Pro Leu Leu
185                 1190                1195                1200

Ser His Phe Ala Glu Thr Val Glu Gly Leu Thr Thr Ile Arg Ala Phe
            1205                1210                1215

Arg Tyr Glu Ala Arg Phe Gln Gln Lys Leu Leu Glu Tyr Thr Asp Ser
        1220                1225                1230

Asn Asn Ile Ala Ser Leu Phe Leu Thr Ala Ala Asn Arg Trp Leu Glu
    1235                1240                1245

Val Arg Met Glu Tyr Ile Gly Ala Cys Val Val Leu Ile Ala Ala Ala
1250                1255                1260

Thr Ser Ile Ser Asn Ser Leu His Arg Glu Leu Ser Ala Gly Leu Val
265                 1270                1275                1280

Gly Leu Gly Leu Thr Tyr Ala Leu Met Val Ser Asn Tyr Leu Asn Trp
            1285                1290                1295

Met Val Arg Asn Leu Ala Asp Met Glu Ile Gln Leu Gly Ala Val Lys
        1300                1305                1310

Gly Ile His Thr Leu Leu Lys Thr Glu Ala Glu Ser Tyr Glu Gly Leu
    1315                1320                1325

Leu Ala Pro Ser Leu Ile Pro Lys Asn Trp Pro Asp Gln Gly Lys Ile
1330                1335                1340

Gln Ile Gln Asn Leu Ser Val Arg Tyr Asp Ser Ser Leu Lys Pro Val
345                 1350                1355                1360

Leu Lys His Val Asn Ala Leu Ile Ser Pro Gly Gln Lys Ile Gly Ile
            1365                1370                1375

Cys Gly Arg Thr Gly Ser Gly Lys Ser Ser Phe Ser Leu Ala Phe Phe
        1380                1385                1390

Arg Met Val Asp Met Phe Glu Gly Arg Ile Ile Ile Asp Gly Ile Asp
    1395                1400                1405

Ile Ala Lys Leu Pro Leu His Thr Leu Arg Ser Arg Leu Ser Ile Ile
1410                1415                1420

Leu Gln Asp Pro Val Leu Phe Ser Gly Thr Ile Arg Phe Asn Leu Asp
425                 1430                1435                1440

Pro Glu Lys Lys Cys Ser Asp Ser Thr Leu Trp Glu Ala Leu Glu Ile
            1445                1450                1455

Ala Gln Leu Lys Leu Val Val Lys Ala Leu Pro Gly Gly Leu Asp Ala
        1460                1465                1470

Ile Ile Thr Glu Gly Gly Glu Asn Phe Ser Gln Gly Gln Arg Gln Leu
    1475                1480                1485

Phe Cys Leu Ala Arg Ala Phe Val Arg Lys Thr Ser Ile Phe Ile Met
1490                1495                1500

Asp Glu Ala Thr Ala Ser Ile Asp Met Ala Thr Glu Asn Ile Leu Gln
505                 1510                1515                1520

Lys Val Val Met Thr Ala Phe Ala Asp Arg Thr Val Val Thr Ile Ala
            1525                1530                1535

His Arg Val His Thr Ile Leu Ser Ala Asp Leu Val Met Val Leu Lys
        1540                1545                1550

Arg Gly Ala Ile Leu Glu Phe Asp Lys Pro Glu Lys Leu Leu Ser Gln
    1555                1560                1565

Lys Asp Ser Val Phe Ala Ser Phe Val Arg Ala Asp Lys
1570                1575                1580

(2) INFORMATION FOR SEQ ID NO:5:
```

(i) SEQUENCE CHARACTERISTICS:
        (A) LENGTH: 1582 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 784874

(xi) SEQUENCE DESCRIPTION: SEQ ID NO:5:

Met Pro Leu Ala Phe Cys Gly Thr Glu Asn His Ser Ala Ala Tyr Arg
 1               5                  10                  15

Val Asp Gln Gly Val Leu Asn Asn Gly Cys Phe Val Asp Ala Leu Asn
            20                  25                  30

Val Val Pro His Val Phe Leu Leu Phe Ile Thr Phe Pro Ile Leu Phe
        35                  40                  45

Ile Gly Trp Gly Ser Gln Ser Ser Lys Val His Ile His His Ser Thr
50                  55                  60

Trp Leu His Phe Pro Gly His Asn Leu Arg Trp Ile Leu Thr Phe Ile
65                  70                  75                  80

Leu Leu Phe Val Leu Val Cys Glu Ile Ala Glu Gly Ile Leu Ser Asp
                85                  90                  95

Gly Val Thr Glu Ser Arg His Leu His Leu Tyr Met Pro Ala Gly Met
            100                 105                 110

Ala Phe Met Ala Ala Ile Thr Ser Val Val Tyr Tyr His Asn Ile Glu
        115                 120                 125

Thr Ser Asn Phe Pro Lys Leu Leu Ile Ala Leu Leu Ile Tyr Trp Thr
130                 135                 140

Leu Ala Phe Ile Thr Lys Thr Ile Lys Phe Val Lys Phe Tyr Asp His
145                 150                 155                 160

Ala Ile Gly Phe Ser Gln Leu Arg Phe Cys Leu Thr Gly Leu Leu Val
                165                 170                 175

Ile Leu Tyr Gly Met Leu Leu Leu Val Glu Val Asn Val Ile Arg Val
            180                 185                 190

Arg Arg Tyr Ile Phe Phe Lys Thr Pro Arg Glu Val Lys Pro Pro Glu
        195                 200                 205

Asp Leu Gln Asp Leu Gly Val Arg Phe Leu Gln Pro Phe Val Asn Leu
210                 215                 220

Leu Ser Lys Gly Thr Tyr Trp Trp Met Asn Ala Phe Ile Lys Thr Ala
225                 230                 235                 240

His Lys Lys Pro Ile Asp Leu Arg Ala Ile Ala Lys Leu Pro Ile Ala
                245                 250                 255

Met Arg Ala Leu Thr Asn Tyr Gln Arg Leu Cys Val Ala Phe Asp Ala
            260                 265                 270

Gln Ala Arg Lys Asp Thr Gln Ser Pro Gln Gly Ala Arg Ala Ile Trp
        275                 280                 285

Arg Ala Leu Cys His Ala Phe Gly Arg Arg Leu Ile Leu Ser Ser Thr
290                 295                 300

Phe Arg Ile Leu Ala Asp Leu Leu Gly Phe Ala Gly Pro Leu Cys Ile
305                 310                 315                 320

Phe Gly Ile Val Asp His Leu Gly Lys Glu Asn His Val Phe Gln Pro
                325                 330                 335

Lys Thr Gln Phe Leu Gly Val Tyr Phe Val Ser Ser Gln Glu Phe Leu
            340                 345                 350

-continued

```
Gly Asn Ala Tyr Val Leu Ala Val Leu Leu Phe Leu Ala Leu Leu Leu
            355                 360                 365
Gln Arg Thr Phe Leu Gln Ala Ser Tyr Val Ala Ile Glu Thr Gly
    370                 375                 380
Ile Asn Leu Arg Gly Ala Ile Gln Thr Lys Ile Tyr Asn Lys Ile Met
385                 390                 395                 400
His Met Ser Thr Ser Asn Leu Ser Met Gly Glu Met Thr Ala Gly Gln
                405                 410                 415
Ile Cys Asn Leu Val Ala Ile Asp Thr Asn Gln Leu Met Trp Phe Phe
            420                 425                 430
Phe Leu Cys Pro Asn Leu Trp Thr Met Pro Val Gln Ile Ile Val Gly
        435                 440                 445
Val Ile Leu Leu Tyr Tyr Ile Leu Gly Val Ser Ala Leu Ile Gly Ala
    450                 455                 460
Ala Val Ile Ile Leu Leu Ala Pro Val Gln Tyr Phe Val Ala Thr Lys
465                 470                 475                 480
Leu Ser Gln Ala Gln Arg Thr Thr Leu Glu His Ser Asn Glu Arg Leu
                485                 490                 495
Lys Gln Thr Asn Glu Met Leu Arg Gly Met Lys Leu Leu Lys Leu Tyr
            500                 505                 510
Ala Trp Glu Ser Ile Phe Cys Ser Arg Val Glu Val Thr Arg Arg Lys
        515                 520                 525
Glu Met Thr Ser Leu Arg Ala Phe Ala Val Tyr Thr Ser Ile Ser Ile
    530                 535                 540
Phe Met Asn Thr Ala Ile Pro Ile Ala Ala Val Leu Ile Thr Phe Val
545                 550                 555                 560
Gly His Val Ser Phe Phe Lys Glu Ser Asp Leu Ser Pro Ser Val Ala
                565                 570                 575
Phe Ala Ser Leu Ser Leu Phe His Ile Leu Val Thr Pro Leu Phe Leu
            580                 585                 590
Leu Ser Ser Val Val Arg Ser Thr Val Lys Ala Leu Val Ser Val Gln
        595                 600                 605
Lys Leu Ser Glu Phe Leu Ser Ser Ala Glu Ile Arg Glu Glu Gln Cys
    610                 615                 620
Ala Pro Arg Glu Pro Ala Pro Gln Gly Gln Ala Gly Lys Tyr Gln Ala
625                 630                 635                 640
Val Pro Leu Lys Val Val Asn Arg Lys Arg Pro Ala Arg Glu Glu Val
                645                 650                 655
Arg Asp Leu Leu Gly Pro Leu Gln Arg Leu Ala Pro Ser Met Asp Gly
            660                 665                 670
Asp Ala Asp Asn Phe Cys Val Gln Ile Ile Gly Gly Phe Phe Thr Trp
        675                 680                 685
Thr Pro Asp Gly Ile Pro Thr Leu Ser Asn Ile Thr Ile Arg Ile Pro
    690                 695                 700
Arg Gly Gln Leu Thr Met Ile Val Gly Gln Val Gly Cys Gly Lys Ser
705                 710                 715                 720
Ser Leu Leu Leu Ala Thr Leu Gly Glu Met Gln Lys Val Ser Gly Ala
                725                 730                 735
Val Phe Trp Asn Ser Asn Leu Pro Asp Ser Glu Gly Arg Gly Pro Gln
            740                 745                 750
Gln Pro Arg Ala Gly Asp Ser Ser Trp Leu Gly Tyr Gln Glu Gln Arg
        755                 760                 765
```

-continued

```
Pro Arg Gly Tyr Ala Ser Gln Lys Pro Trp Leu Leu Asn Ala Thr Val
    770                 775                 780
Glu Glu Asn Ile Thr Phe Glu Ser Pro Phe Asn Pro Gln Arg Tyr Lys
785                 790                 795                 800
Met Val Ile Glu Ala Cys Ser Leu Gln Pro Asp Ile Asp Ile Leu Pro
                805                 810                 815
His Gly Asp Gln Thr Gln Ile Gly Glu Arg Gly Ile Asn Leu Ser Gly
                820                 825                 830
Gly Gln Arg Pro Asp Gln Cys Gly Pro Glu Pro Ser Thr Ser Arg Pro
                835                 840                 845
Met Phe Val Phe Leu Asp Asp Pro Phe Ser Ala Leu Asp Val His Leu
850                 855                 860
Ser Asp His Leu Met Gln Ala Gly Ile Leu Glu Leu Leu Arg Asp Asp
865                 870                 875                 880
Lys Arg Thr Val Val Leu Val Thr His Lys Leu Gln Tyr Leu Pro His
                885                 890                 895
Ala Asp Trp Ile Ile Ala Met Lys Asp Gly Thr Ile Gln Arg Glu Gly
                900                 905                 910
Thr Leu Lys Asp Phe Gln Arg Ser Glu Cys Gln Leu Phe Glu His Trp
                915                 920                 925
Lys Thr Leu Met Asn Arg Gln Asp Gln Glu Leu Glu Lys Glu Thr Val
                930                 935                 940
Met Glu Arg Lys Ala Ser Glu Pro Ser Gln Gly Leu Pro Arg Ala Met
945                 950                 955                 960
Ser Ser Arg Asp Gly Leu Leu Leu Asp Glu Glu Glu Glu Glu Glu Glu
                965                 970                 975
Ala Ala Glu Ser Glu Glu Asp Asp Asn Leu Ser Ser Val Leu His Gln
                980                 985                 990
Arg Ala Lys Ile Pro Trp Arg Ala Cys Thr Lys Tyr Leu Ser Ser Ala
                995                 1000                1005
Gly Ile Leu Leu Leu Ser Leu Leu Val Phe Ser Gln Leu Leu Lys His
    1010                1015                1020
Met Val Leu Val Ala Ile Asp Tyr Trp Leu Ala Lys Trp Thr Asp Ser
025                 1030                1035                1040
Ala Leu Val Leu Ser Pro Ala Ala Arg Asn Cys Ser Leu Ser Gln Glu
                1045                1050                1055
Cys Asp Leu Asp Gln Ser Val Tyr Ala Met Val Phe Thr Leu Leu Cys
                1060                1065                1070
Ser Leu Gly Ile Val Leu Cys Leu Val Thr Ser Val Thr Val Glu Trp
                1075                1080                1085
Thr Gly Leu Lys Val Ala Lys Arg Leu His Arg Ser Leu Leu Asn Arg
    1090                1095                1100
Ile Ile Leu Ala Pro Met Arg Phe Phe Glu Thr Thr Pro Leu Gly Ser
105                 1110                1115                1120
Ile Leu Asn Arg Phe Ser Ser Asp Cys Asn Thr Ile Asp Gln His Ile
                1125                1130                1135
Pro Ser Thr Leu Glu Cys Leu Ser Arg Ser Thr Leu Leu Cys Val Ser
            1140                1145                1150
Ala Leu Thr Val Ile Ser Tyr Val Thr Pro Val Phe Leu Val Ala Leu
    1155                1160                1165
Leu Pro Leu Ala Val Val Cys Tyr Phe Ile Gln Lys Tyr Phe Arg Val
    1170                1175                1180
Ala Ser Arg Asp Leu Gln Gln Leu Asp Asp Thr Thr Gln Leu Pro Leu
```

-continued

```
185              1190           1195              1200

Val Ser His Phe Ala Glu Thr Val Glu Gly Leu Thr Thr Ile Arg Ala
            1205           1210              1215

Phe Arg Tyr Glu Ala Arg Phe Gln Gln Lys Leu Leu Glu Tyr Thr Asp
            1220           1225              1230

Ser Asn Asn Ile Ala Ser Leu Phe Leu Thr Ala Ala Asn Arg Trp Leu
            1235           1240              1245

Glu Val Cys Met Glu Tyr Ile Gly Ala Cys Val Val Leu Ile Ala Ala
1250           1255              1260

Ala Thr Ser Ile Ser Asn Ser Leu His Arg Glu Leu Ser Ala Gly Leu
265            1270              1275              1280

Val Gly Leu Gly Leu Thr Tyr Ala Leu Met Val Ser Asn Tyr Leu Asn
            1285           1290              1295

Trp Met Val Arg Asn Leu Ala Asp Met Glu Ile Gln Leu Gly Ala Val
            1300           1305              1310

Lys Arg Ile His Ala Leu Leu Lys Thr Glu Ala Glu Ser Tyr Glu Gly
            1315           1320              1325

Leu Leu Ala Pro Ser Leu Ile Pro Lys Asn Trp Pro Asp Gln Gly Lys
    1330           1335              1340

Ile Gln Ile Gln Asn Leu Ser Val Arg Tyr Asp Ser Ser Leu Lys Pro
345            1350              1355              1360

Val Leu Lys His Val Asn Thr Leu Ile Ser Pro Gly Gln Lys Ile Gly
            1365           1370              1375

Ile Cys Gly Arg Thr Gly Ser Gly Lys Ser Ser Phe Ser Leu Ala Phe
            1380           1385              1390

Phe Arg Met Val Asp Met Phe Glu Gly Arg Ile Ile Ile Asp Gly Ile
            1395           1400              1405

Asp Ile Ala Lys Leu Pro Leu His Thr Leu Arg Ser Arg Leu Ser Ile
    1410           1415              1420

Ile Leu Gln Asp Pro Val Leu Phe Ser Gly Thr Ile Arg Phe Asn Leu
425            1430              1435              1440

Asp Pro Glu Lys Lys Cys Ser Asp Ser Thr Leu Trp Glu Ala Leu Glu
            1445           1450              1455

Ile Ala Gln Leu Lys Leu Val Val Lys Ala Leu Pro Gly Gly Leu Asp
            1460           1465              1470

Ala Ile Ile Thr Glu Gly Gly Glu Asn Phe Ser Gln Gly Gln Arg Gln
    1475           1480              1485

Leu Phe Cys Leu Ala Arg Ala Phe Val Arg Lys Thr Ser Ile Phe Ile
    1490           1495              1500

Met Asp Glu Ala Thr Ala Ser Ile Asp Met Ala Thr Glu Asn Ile Leu
505            1510              1515              1520

Gln Lys Val Val Met Thr Ala Phe Ala Asp Arg Thr Val Val Thr Ile
            1525           1530              1535

Ala His Arg Val His Thr Ile Leu Ser Ala Asp Leu Val Met Val Leu
            1540           1545              1550

Lys Arg Gly Ala Ile Leu Glu Phe Asp Lys Pro Glu Thr Leu Leu Ser
            1555           1560              1565

Gln Lys Asp Ser Val Phe Ala Ser Phe Val Arg Ala Asp Lys
    1570           1575              1580
```

HUMAN SULFONYLUREA RECEPTOR

This application is a divisional application of U.S. application Ser. No. 08/726,320, filed Oct. 2, 1996.

FIELD OF THE INVENTION

The present invention relates to nucleic acid and amino acid sequences of a novel human sulfonylurea receptor and to the use of these sequences in the diagnosis, study, prevention and treatment of disease.

BACKGROUND OF THE INVENTION

ATP-dependent potassium ($K_{ATP}$) channels serve to couple metabolic state to electrical activity in many types of cells. By hyperpolarizing the cell, $K_{ATP}$ channels limit electrical activity and hence reduce $Ca^{2+}$ entry into muscle and nerve cells. In the pancreas, they are a critical link between blood glucose concentration and insulin secretion.

Sulfonylureas (SUs) are oral hypoglycemics widely used in the treatment of non-insulin dependent diabetes mellitus (NIDDM). SUs stimulate insulin release from pancreatic islet α cells. The mechanism for insulin release involves 1) inhibition of a $K_{ATP}$ channel which sets the β cell resting membrane potential, 2) reduction of $K^+$ outflow which causes β cell depolarization and 3) the activation of one or more voltage-dependent L-type calcium channels which results in $Ca^{2+}$ influx, exocytosis, and insulin release. SUs such as tolbutamide or glyburide decrease $K_{ATP}$ channel activity, thereby depolarizing the cell and triggering insulin release.

Until recently the $K_{ATP}$ channel and the sulfonylurea receptor (SUR) were thought to be the same molecule (Aguilar-Bryan et al (1995) Science 268:423–426); however, SUR does not possess intrinsic $K^+$ channel activity (Ammala C et al (1996) Nature 379:545–548). Instead SUR interacts with inward-rectifier $K^+$ channels, conferring SU and ATP sensitivity to and modulating the activity of these channels (Inagaki N et al (1995) Science 270: 1166–1170).

A second isoform of SUR, denoted SUR2, has recently been discovered in rat. This isoform has different tissue distribution and different SU and ATP binding properties from rat SUR (Inagaki N et al (1996) Neuron 16:1011–1017). The channel kinetics of Kir6.2, an inward-rectifier $K^+$ channel, co-expressed with SUR2 are different than the channel kinetics of Kir6.2 co-expressed with SUR. Based on these observations, it is suggested that a family of structurally related but functionally distinct SURs determine the ATP sensitivity and pharmacological responses of KAT, channels in various tissues (Inagaki N et al (1996), supra).

SURs from rat and hamster consist of 1581 and 1582 amino acids, respectively, with 12 potential membrane-spanning helices (Aguilar-Bryan et al, supra). In addition, the proteins contain two domains having strong similarity to the nucleotide binding folds (NBFs) of the ATP-binding cassette (ABC) superfamily of proteins. The proposed topology of the rat, hamster, and a recently reported human SUR (GenBank GI 1369844; unpublished) consists of an external amino terminus, nine predicted transmembrane helices, the first cytosolic NBF (NBF-1), four more transmembrane helices, the second cytosolic NBF (NBF-2) and a cytosolic C-terminus. The topology of the SURs are similar to other members of the ABC superfamily including multidrug resistance (MDR) proteins and cystic fibrosis transmembrane regulators (CFTR; Philipson LH and Steiner DF (1995) Science 268:372–373).

Ad The NBFs of ABC superfamily proteins control activity through their interaction with cytosolic nucleotides. In cystic fibrosis, the more frequent and severe disease mutations are located in the nucleotides encoding the two NBFs of the CFTR protein (Tsui L-C (1992) Trends Genet 8:392). Familial persistent hyperinsulinemic hypoglycemia of infancy (PHHI) may be caused by mutations affecting NBF-2 of SUR (Thomas PM et al (1995) Science 268:426–429).

SU-sensitive $K_{ATP}$ channels are present in brain cells and play a role in neurosecretion at nerve terminals. $K_{ATP}$ channels in the substantia nigra, a brain region that shows high SU binding, are inhibited by high glucose concentrations and antidiabetic SUs, and are activated by ATP depletion and anoxia. Furthermore, inhibition of the KAT, channel activates gamma-aminobutyric acid (GABA) release, whereas $K_{ATP}$ channel activation inhibits GABA release (Amoroso S et al (1990) Science 247:852–854; Schmidt-Antomarchi et al (1990) Proc Natl Acad Sci USA 87:3489–3492).

Action potentials in cardiac cells are modulated by SU compounds binding to SURs. The duration of the action potential of guinea pig cardiac cells was drastically reduced by decreasing intracellular ATP concentrations ($[ATP]_{in}$) by perfusion or by blockade of oxidative phosphorylation. Glibenclamide, an SU compound, was found to restore normal or nearly normal action potentials in these $[ATP]_{in}$-depleted cardiac cells. (Fosset M et al (1988) J Biol Chem 263:7933–7936). Restoration was attributed to inhibition of cardiac $K_{ATP}$ channels by sulfonylurea compounds acting via the SURs.

SURs confer ATP and SU sensitivity to inwardly-rectifying potassium channels, thereby coupling metabolic state to electrical activity in tissues such as brain, pancreas, and heart. SURs are useful in the diagnosis and treatment of diseases related to abnormal $K_{ATP}$ channel function, such as NIDDM and PHHI. The selective modulation of the expression or activities of SURs may allow the successful management of such diseases.

SUMMARY OF THE INVENTION

The present invention discloses a human sulfonylurea receptor protein, hereinafter referred to as SURH, having chemical and structural homology to the SUR protein from rat and hamster. Accordingly, the invention features a substantially purified SURH, having the amino acid sequence of SEQ ID NO:1 and the structural characteristics of SURs.

One aspect of the invention features isolated and substantially purified polynucleotides which encode SURH. In a particular aspect, the polynucleotide is the nucleotide sequence of SEQ ID NO:2. In another aspect, the polynucleotide is the nucleotide sequence extending from $T_{2780}$ to $A_{2923}$ of SEQ ID NO:2.

The invention also relates to a polynucleotide sequence comprising the complement of SEQ ID NO:2 or variants thereof. In addition, the invention features nucleotide sequences which hybridize under stringent conditions to SEQ ID NO:2.

The present invention also relates to an expression vector which contains polynucleotides encoding SURH, and the use of said vector to transform or transfect host cells or organisms. The invention also features methods for producing SURH. The present invention also relates to antibodies which bind specifically to SURH polypeptides, and to agonists and antagonists of SURH. The present invention also relates to pharmaceutical compositions comprising SURH, fragments thereof, agonists of SURH, or antagonists of SURH, in conjunction with a suitable pharmaceutical carrier.

BRIEF DESCRIPTION OF THE FIGURES

FIGS. 1A–1G show the amino acid sequence (SEQ ID NO:1) and the nucleic acid sequence (SEQ ID NO:2) of the human sulfonylurea receptor protein SURH, produced using MACDNAIS software (Hitachi Software Engineering Co Ltd).

FIGS. 2A–2D show the amino acid sequence alignments among SURH (SEQ ID NO:1), a human SUR isoform (GI 1369844; SEQ ID NO:3), SUR from Norway rat (GI 13115343; SEQ ID NO:4), and SUR from black-bellied hamster (GI 784874; SEQ ID NO:5) produced using the multisequence alignment program of DNASTAR software (DNAStar Inc, Madison Wis.).

DETAILED DESCRIPTION OF THE INVENTION

Definitions

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to peptide or protein sequence.

"Consensus" as used herein may refer to a nucleic acid sequence 1) which has been resequenced to resolve uncalled bases, 2) which has been extended using XL-PCR (Perkin Elmer, Norwalk Conn.) in the 5' and/or the 3' direction and resequenced, 3) which has been assembled from the overlapping sequences of more than one Incyte clone GCG Fragment Assembly System, (GCG, Madison Wis.), or 4) which has been both extended and assembled.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

A "variant" of SURH is defined as an amino acid sequence that is different by one or more amino acid substitutions. The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring SURH.

A "substitution" results from the replacement of one or more nucleotides or amino acids by different nucleotides or amino acids, respectively.

The term "biologically active" refers to a SURH having structural, regulatory or biochemical functions of the naturally occurring SURH. Likewise, "immunologically active" defines the capability of the natural, recombinant or synthetic SURH, or any oligopeptide thereof, to induce a specific immune response in appropriate animals or cells and to bind with specific antibodies.

The term "agonist" refers to a molecule which, when bound to SURH, causes a change in SURH which modulates the biological activity of SURH.

The term "antagonist" refers to a molecule which, when bound to SURH, blocks the binding of an agonist to SURH, which prevents the agonist-induced change in the biological activity of SURH. Agonists and antagonists may include proteins, nucleic acids, carbohydrates, or other molecules which bind to SURH.

The term "modulate" as used herein refers to a change or an alteration in the biological activity of SURH. Modulation may be an increase or a decrease in biological activity, a change in binding characteristics, or any other change in the biological properties of SURH.

The term "derivative" as used herein refers to the chemical modification of a nucleic acid encoding SURH or the encoded SURH. Illustrative of such modifications would be replacement of hydrogen by an alkyl, acyl, or amino group. A nucleic acid derivative would encode a polypeptide which retains essential biological characteristics of natural SURH.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

"Stringency" typically occurs in a range from about Tm-5° C. (5° C. below the Tm of the probe) to about 20° C. to 25° C. below Tm. As will be understood by those of skill in the art, a stringency hybridization can be used to identify or detect identical polynucleotide sequences or to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies is described in Dieffenbach CW and GS Dveksler (1995, *PCR Primer, a Laboratory Manual*, Cold Spring Harbor Press, Plainview N.Y.).

Preferred Embodiments The invention relates to a human sulfonylurea receptor protein, SURH, initially identified among the cDNAs from a library constructed from human brain tissue (BRAINOT03) and to the use of the nucleic acid and amino acid sequences disclosed herein in the study, diagnosis, prevention and treatment of disease. Northern analysis using the LIFESEQ™ database (Incyte Pharmaceuticals, Palo Alto Calif.) indicates that SURH-encoding nucleotide sequences are most abundantly transcribed in brain, and are also found in pancreas, breast, uterus and prostate. It must be noted that naturally occurring expression of SURH is not necessarily limited to these tissues.

The invention also encompasses SURH variants. A preferred SURH variant is one having at least 80% amino acid sequence similarity to the SURH amino acid sequence (SEQ ID NO:1), a more preferred SURH variant is one having at least 90% amino acid sequence similarity to SEQ ID NO:1 and a most preferred SURH variant is one having at least 95% amino acid sequence similarity to SEQ ID NO:1.

The nucleic acid sequence encoding SURH was first identified in the cDNA, Incyte Clone 662342, through a computer-generated search for amino acid sequence alignments. The consensus nucleotide sequence, SEQ ID NO:2, disclosed herein (FIGS. 1A–1G) encodes the amino acid sequence, SEQ ID NO:1, designated SURH. The consensus nucleotide sequence was extended and assembled from Incyte Clones 1270543 (BRAINOT09); 1332410 (PANCNOT07); 640147 (BRSTNOT03); 641239 (BRSTNOT03); 662342 (BRAINOT03); and 952281 (PANCNOT05) from the LIFESEQ™ database (Incyte Pharmaceuticals, Palo Alto Calif.).

The present invention is based in part on the chemical homology shown in FIGS. 2A–2D, among SURH and an SUR isoform from human (GI 1369844, unpublished), and a SUR homologs from rat (GI 13115343; Aguilar-Bryan et al, supra) and hamster (GI 784874; Aguilar-Bryan et al, supra). The human isoform, the rat homolog and the hamster homolog have, respectively, 96%, 92% and 90% amino acid sequence identity to SURH.

The SURH protein sequence consists of 1580 amino acids. From the amino acid sequence alignments (FIGS. 2A–2D) and its hydrophobicity, SURH contains twelve potential membrane-spanning helices located at or near residues 31–51, 75–94, 135–155, 169–189, 306–323, 350–368, 448–469, 540–560, 576–596, 1002–1020, 1063–1076, 1154–1172, and 1276–1296. Furthermore, the protein contains two nucleotide binding fold (NBF) domains encompassing residues 695–893 (NBF-1) and 1356–1534 (NBF-2). The predicted topology of SURH consists of an extracellular amino terminus, nine transmembrane helices, cytosolic NBF-1, four transmembrane helices and cytosolic NBF-2 culminating at the cytosolic C-terminus. In addition, the SURH protein sequence contains 11 potential N-glycosylation sites. Four of these potential N-glycosylation sites, $N_{10}$, $N_{405}$, $N_{104}$, and $N_{1048}$, reside on predicted extracellular-facing surface loops. As shown is FIG. 2E, the SURH amino acid sequence at positions 913 to 923, 925 to 943 and 952 to 960, in the region between NBF-1 and the tenth predicted transmembrane helix, have no identity with the corresponding amino acid residues in a human SUR isoform (GI 1369844).

The SURH Coding Sequences

The assembled nucleic acid and deduced amino acid sequences of SURH are shown in FIGS. 1A–1G. In accordance with the invention, any nucleic acid sequence which encodes the amino acid sequence of SURH can be used to generate recombinant molecules which express SURH. In a specific embodiment described herein, a partial sequence encoding SURH was first isolated as Incyte Clone 662342 from a human brain tissue cDNA library (BRAINOT03).

As noted above, there is minimal amino acid sequence identity between a human SUR isoform (GI 1369844) and SURH between amino acids $S_{913}$ to $R_{960}$ of SEQ ID NO:1, which corresponds to nucleotides $T_{2780}$ to $A_{2923}$ of SEQ ID NO:2. Oligonucleotides complementary to this region of SEQ ID NO:2 are highly specific for the SURH of the present invention. Such oligonucleotides are useful for diagnostic and therapeutic applications specific to SURH.

It will be appreciated by those skilled in the art that as a result of the degeneracy of the genetic code, a multitude of SURH-encoding nucleotide sequences, some bearing minimal homology to the nucleotide sequences of any known and naturally occurring gene, may be produced. The invention contemplates each and every possible variation of nucleotide sequence that could be made by selecting combinations based on possible codon choices. These combinations are made in accordance with the standard triplet genetic code as applied to the nucleotide sequence of naturally occurring SURH, and all such variations are to be considered as being specifically disclosed.

Although nucleotide sequences which encode SURH and its variants are preferably capable of hybridizing to the nucleotide sequence of the naturally occurring SURH under appropriately selected conditions of stringency, it may be advantageous to produce nucleotide sequences encoding SURH or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding SURH and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a SURH and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a gene encoding SURH.

Also included within the scope of the present invention are polynucleotide sequences that are capable of hybridizing to the nucleotide sequences of FIGS. 1A–1G under various conditions of stringency. Hybridization conditions are based on the melting temperature (Tm) of the a nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and may be used at a defined stringency.

Altered nucleic acid sequences encoding SURH which may be used in accordance with the invention include deletions, insertions or substitutions of different nucleotides resulting in a polynucleotide that encodes the same or a functionally equivalent SURH. The protein may also show deletions, insertions or substitutions of amino acid residues which produce a silent change and result in a functionally equivalent SURH. Deliberate amino acid substitutions may be made on the basis of similarity in polarity, charge, solubility, hydrophobicity, hydrophilicity, and/or the amphipathic nature of the residues as long as the biological activity of SURH is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of SURH. As used herein, an "allele" or "allelic sequence" is an alternative form of SURH. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE® US Biochemical Corp, Cleveland Ohio), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence encoding SURH may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Another method which may be used to retrieve unknown sequences is that of Parker JD et al (1991; Nucleic Acids Res 19:3055–60). Additionally, one can use PCR, nested primers and PromoterFinder libraries to walk in genomic DNA (PROMOTERFINDER Clontech (Palo Alto Calif.). This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5' nontranslated regulatory region.

Capillary electrophoresis may be used to analyze the size or confirm the nucleotide sequence of sequencing or PCR products. Systems for rapid sequencing are available from Perkin Elmer, Beckman Instruments (Fullerton Calif.), and other companies. Capillary sequencing may employ flowable polymers for electrophoretic separation, four different fluorescent dyes (one for each nucleotide) which are laser activated, and detection of the emitted wavelengths by a charge coupled device camera. Output/light intensity is converted to electrical-signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Expression of the Nucleotide Sequence

In accordance with the present invention, polynucleotide sequences which encode SURH, fragments of the polypeptide, fusion proteins or functional equivalents thereof may be used in recombinant DNA molecules that direct the expression of SURH in appropriate host cells. Due to the inherent degeneracy of the genetic code, other DNA sequences which encode substantially the same or a functionally equivalent amino acid sequence, may be used to clone and express SURH. As will be understood by those of skill in the art, it may be advantageous-to produce SURH-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of SURH expression or to produce recombinant RNA transcripts having desirable properties, such as a longer half-life, than transcripts produced from naturally occurring sequence.

The nucleotide sequences of the present invention can be engineered in order to alter a coding sequence of SURH for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant nucleotide sequence encoding SURH may be ligated to a heterologous sequence to encode a fusion protein. For example, for screening of peptide libraries for inhibitors of SURH activity, it may be useful to encode a chimeric SURH protein that is recognized by a commercially available antibody. A fusion protein may also be engineered to contain a cleavage site located between a SURH sequence and the heterologous protein sequence, so that the SURH may be cleaved and substantially purified away from the heterologous moiety.

In an alternate embodiment of the invention, the coding sequence for SURH may be synthesized, whole or in part, using chemical methods well known in the art (see Caruthers M H et al (1980) Nuc Acids Res Symp Ser 215–23, Horn T et al(1980) Nuc Acids Res Symp Ser 225–32, etc). Alternatively, the protein itself could be produced using chemical methods to synthesize a SURH amino acid sequence, whole or in part. For example, peptide synthesis can be performed using various solid-phase techniques (Roberge J Y et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures van Molecular Principles*, WH Freeman and Co, New York N.Y.). The composition of the synthetic peptides may be confirmed by amino acid analysis or sequencing (eg, the Edman degradation procedure; Creighton, supra). Additionally the amino acid sequence of SURH, or any part thereof, may be altered during direct synthesis and/or combined using chemical methods with sequences from other proteins, or any part thereof, to produce a variant polypeptide.

Expression Systems

In order to express a biologically active SURH, the nucleotide sequence encoding SURH or its functional equivalent is inserted into an appropriate expression vector, ie, a vector which contains the necessary elements for the transcription and translation of the inserted coding sequence.

Methods which are well known to those skilled in the art can be used to construct expression vectors containing a SURH coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual*, Cold Spring Harbor Press, Plainview N.Y. and Ausubel F M et al (1989) *Current Protocols in Molecular Biology*, John Wiley & Sons, New York NY.

A variety of expression vector/host systems may be utilized to contain and express a SURH coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacz promoter of the BLUE-SCRIPT phagemid (Stratagene, LaJolla Calif.) or PSPORT 1 (Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of SURH, vectors based on SV40 or EBV may be used with an appropriate selectable marker.

In bacterial systems, a number of expression vectors may be selected depending upon the use intended for SURH. For example, when large quantities of SURH are needed for the induction of antibodies, vectors which direct high level expression of fusion proteins that are readily purified may be desirable. Such vectors include, but are not limited to, the multifunctional *E. coli* cloning and expression vectors such as BLUESCRIPT (Stratagene), in which the SURH coding sequence may be ligated into the vector in frame with sequences for the amino-terminal Met and the subsequent 7 residues of 3-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase and PGH may be used. For reviews, see Ausubel et al (supra) and Grant et al (1987) Methods in Enzymology 153:516–544. In cases where plant expression vectors are used, the expression of a sequence encoding SURH may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry LE in McGraw Hill *Yearbook of Science and Technology* (1992) McGraw Hill New York NY, pp 191–196 or Weissbach and Weissbach (1988) *Methods for Plant Molecular Biology*, Academic Press, New York N.Y., pp 421–463.

An alternative expression system which could be used to express SURH is an insect system. In one such system, *Autographa californica* nuclear polyhedrosis virus (AcNPV) is used as a vector to express foreign genes in *Spodoptera frugiperda* cells or in Trichoplusia larvae. The SURH coding sequence may be cloned into a nonessential region of the virus, such as the polyhedrin gene, and placed under control of the polyhedrin promoter. Successful insertion of the SURH coding sequence will render the polyhedrin gene inactive and produce recombinant virus lacking coat protein. The recombinant viruses are then used to infect *S. frugiperda* cells or Trichoplusia larvae in which SURH is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a coding sequence for SURH may be ligated into an adenovirus transcription/translation complex consisting of the late promoter and tripartite leader sequence. Insertion in a nonessential El or E3 region of the viral genome will result in a viable virus capable of expressing SURH in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a SURH sequence. These signals include the ATG initiation codon and adjacent sequences. In cases where nucleic acid encoding SURH, its initiation codon and upstream sequences are inserted into the appropriate expression vector, no additional translational control signals may be needed. However, in cases where only coding sequence, or a portion thereof, is inserted, exogenous translational control signals including the ATG initiation codon must be provided. Furthermore, the initiation codon must be in the correct reading frame to ensure translation of the entire insert. Exogenous translational elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express SURH may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt-cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, 8 glucuronidase and its substrate, GUS, and luciferase and its substrate, luciferin, being widely used not only to identify transformants, but also to quantify the amount of transient or stable protein expression attributable to a specific vector system (Rhodes C A et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the SURH polynucleotide sequence is inserted within a marker gene sequence, recombinant cells containing SURH can be identified by the absence of marker gene function. Alternatively, a marker gene can be placed in tandem with a SURH sequence under the control of a single promoter. Expression of the marker gene in response to induction or selection usually indicates expression of the tandem SURH as well.

Alternatively, host cells which contain the coding sequence for SURH and express SURH may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the polynucleotide sequence encoding SURH can be detected by DNA-DNA or DNA-RNA hybridization or amplification using probes, portions or fragments of SURH-encoding nucleotides. Nucleic acid amplification based assays involve the use of oligonucleotides or oligomers based on the SURH sequence to detect transformants containing SURH DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of SURH, using either polyclonal or monoclonal antibodies specific for the protein are known in the art. Examples-include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SURH is preferred, but a competitive binding assay may be employed. These and other assays are described, among other places, in Hampton R et al (1990, *Serological Methods, a Laboratory Manual*, APS Press, St Paul Minn.) and Maddox DE et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to SURH include oligolabeling, nick translation, end-labeling or PCR amplification using a labeled nucleotide. Alternatively, the SURH sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277, 437; 4,275,149 and 4,366,241. Also, recombinant immunoglobulins may be produced as shown in U.S. Pat. No. 4,816,567 incorporated herein by reference.

Purification of SURH

Host cells transformed with a SURH-encoding nucleotide sequence may be cultured under conditions suitable for the expression and recovery of the encoded protein from cell culture. The protein produced by a recombinant cell may be contained intracellularly or secreted depending on the sequence and/or the vector used. As will be understood by those of skill in the art, expression vectors containing SURH can be designed for efficient production and proper transmembrane insertion of SURH into a prokaryotic or eukaryotic cell membrane. Other recombinant constructions may join SURH to nucleotide sequence encoding a polypeptide domain which will facilitate purification of soluble proteins (Kroll DJ et al (1993) DNA Cell Biol 12:441–53; cf discussion of vectors infra containing fusion proteins).

SURH may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of cleavable linker sequences such as Factor XA or enterokinase (Invitrogen, San Diego Calif.) between the purification domain and SURH is useful to facilitate purification. One such expression vector provides for expression of a fusion protein compromising an SURH and contains nucleic acid encoding 6 histidine residues followed by thioredoxin and an enterokinase cleavage site. The histidine residues facilitate purification on IMIAC (immobilized metal ion affinity chromatography) as described in Porath et al (1992) Protein Expression and Purification 3: 263–281) while the enterokinase cleavage site provides a means for purifying the protein from the fusion protein.

In addition to recombinant production, fragments of SURH may be produced by direct peptide synthesis using solid-phase techniques (cf Stewart et al (1969) *Solid-Phase Peptide Synthesis*, WH Freeman Co, San Francisco; Merrifield J (1963) J Am Chem Soc 85:2149–2154). 1 vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of SURH may be chemically synthesized separately and combined using chemical methods to produce the full length molecule.

Use of SURH

The rationale for the use of polypeptide and polynucleotide sequences disclosed herein is based in part on the chemical and structural homology among SURH and a human isoform, a rat homolog and a hamster homolog of SUR.

The SUR/$K_{ATP}$ channel complex plays a role in neurosecretion and is implicated in the response of the brain to hyper- and hypoglycemia and ischemia. In the pancreas, it is a critical link between blood glucose concentration and insulin secretion. In cardiac cells, action potentials are modulated by sulfonylurea (SU) compounds binding to SURs. Accordingly, SURH may be used in the diagnosis and treatment of diseases and conditions such as, but not limited to, type II diabetes (NIDDM), hyper- and hypoglycemia (including PHHI), cardiac impulse disorders (such as arrhythmias and tachycardias), and other disorders relating to SUR and the SUR/$K_{ATP}$ channel complex.

Some SU therapeutics, while highly effective in the treatment of NIDDM and related disorders, have adverse side-effects. SUs can cause severe and prolonged hypoglycemia, requiring massive glucose infusions and hospitalization for several days. In addition, some SUs can cause skin lesions, including drug-induced erythroderma (exfoliative dermatitis). The isolated SURH protein or its fragments may therefore be useful as a target in drug discovery programs to screen for novel therapeutic molecules with, for example, more desirable binding characteristics, more efficacious metabolic lifetimes, or fewer or less debilitating side-effects than conventional SU therapeutics.

SURH or its fragments may be used to identify other specific molecules with which it binds such as agonists or antagonists.

SURH-specific antibodies are useful for the diagnosis and treatment of conditions and diseases associated with expression of the polypeptides. Antibodies specifically recognizing SURH may be used to quantitate SURH for diagnostic purposes. Therapeutic antibodies may be used to block or modify the interactions between SUs and SURH, or SURH and $K_{ATP}$ channel, in order to treat diseases or conditions associated with SURH and/or the $K_{ATP}$ channel.

In some instances it may be advantageous to suppress SURH expression. Expression of mutant SURH sequences may be suppressed by administration of SURH antisense oligonucleotides.

The SURH nucleic acid sequence of SEQ ID NO:2 can be incorporated into effective eukaryotic expression vectors and directly administered into somatic cells for gene therapy. In like manner, RNA transcripts produced in vitro may be encapsulated in and administered via liposomes. Such vectors and transcripts may function transiently or may be incorporated into the host chromosomal DNA for longer term expression.

In vivo delivery of genetic constructs into subjects is developed to the point of targeting specific cell types. The delivery to specific cells has been accomplished, for instance, by complexing nucleic acids with proteinous ligands that recognize cell specific receptors which mediate uptake (cf Wu G Y et al (1991) J Biol Chem 266:14338–42). Alternatively, recombinant nucleic acid constructs may be injected directly for local uptake and integration (Jiao S et al (1992) Human Gene Therapy 3:21–33).

SURE Antibodies

SURH-specific antibodies are useful for the diagnosis of conditions and diseases associated with expression of SURH. Such antibodies may include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

SURH for antibody induction does not require biological activity; however, the protein fragment, or oligopeptide must be antigenic. Peptides used to induce specific antibodies may have an amino acid sequence consisting of at least five amino acids, preferably at least 10 amino acids. Preferably, they should mimic a portion of the amino acid sequence of the natural protein and may contain the entire amino acid sequence of a small, naturally occurring molecule. Short stretches of SURH amino acids may be fused with those of another protein such as keyhole limpet hemocyanin and antibody produced against the chimeric molecule. Procedures well known in the art can be used for the production of antibodies to SURH.

For the production of antibodies, various hosts including goats, rabbits, rats, mice, etc may be immunized by injection with SURH or any portion, fragment or oligopeptide which retains immunogenic properties. Depending on the host species, various adjuvants may be used to increase immunological response. Such adjuvants include but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to SURH may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy*, Alan R Liss Inc, New York NY, pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce SURH-specific single chain antibodies.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for SURH may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse WD et al (1989) Science 256:1275–1281).

A variety of protocols for competitive binding or immunoradiometric assays using either polyclonal or monoclonal antibodies with established specificities are well known in the art. Such immunoassays typically involve the formation of complexes between SURH and its specific antibody and the measurement of complex formation. A two-site, monoclonal-based immunoassay utilizing monoclonal antibodies reactive to two noninterfering epitopes on a specific SURH protein is preferred, but a competitive binding assay may also be employed. These assays are described in Maddox DE et al (1983, J Exp Med 158:1211).

Diagnostic Assays Using SURH Specific Antibodies

Particular SURH antibodies are useful for the diagnosis of conditions or diseases characterized by expression of SURH or in assays to monitor patients being treated with SURH, agonists or inhibitors. Diagnostic assays for SURH include methods utilizing the antibody and a label to detect SURH in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring SURH, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on SURH is preferred, but a competitive binding assay may be employed. These assays are described, among other places, in Maddox, D E et al (1983, J Exp Med 158:1211).

In order to provide a basis for diagnosis, normal or standard values for SURH expression must be established. This is accomplished by combining body fluids or cell extracts taken from normal subjects, either animal or human, with antibody to SURH under conditions suitable for complex formation which are well known in the art. The amount of standard complex formation may be quantified by comparing various artificial membranes containing known quantities of SURH with both control and disease samples from biopsied tissues. Then, standard values obtained from normal samples may be compared with values obtained from samples from subjects potentially affected by disease. Deviation between standard and subject values establishes the presence of disease state.

Drug Screening

SURH, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between SURH and the agent being tested, may be measured.

Another technique for drug screening which may be used for high throughput screening of compounds having suitable binding affinity to the SURH is described in detail in "Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of SURH and washed. Bound SURH is then detected by methods well known in the art. Substantially purified SURH can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding SURH specifically compete with a test compound for binding SURH. In this manner, the antibodies can be used to detect the presence of any peptide which shares one or more antigenic determinants with SURH.

Uses of the Polynucleotide Encoding SURH

A polynucleotide encoding SURH, or any part thereof, may be used for diagnostic and/or therapeutic purposes. For diagnostic purposes, the SURH of this invention may be used to detect and quantitate gene expression in biopsied tissues in which expression of SURH may be implicated. The diagnostic assay is useful to distinguish between absence, presence, and excess expression of SURH and to monitor regulation of SURH levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding SURH or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring SURH, alleles or related sequences.

Probes may also be used for the detection of related sequences and should preferably contain at least 50% of the nucleotides from any of these SURH encoding sequences. The hybridization probes of the subject invention may be derived from the nucleotide sequence of SEQ ID NO:2 or from genomic sequence including promoter, enhancer elements and introns of the naturally occurring SURH. Hybridization probes many be labeled by a variety of reporter groups, including radionuclides such as $^{32}$P or $^{35}$S, or enzymatic labels such as alkaline phosphatase coupled to the probe via avidin/biotin coupling systems, and the like.

Other means for producing specific hybridization probes for SURH DNAs include the cloning of nucleic acid sequences encoding SURH or SURH derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostic Use

Polynucleotide sequences encoding SURH may be used for the diagnosis of conditions or diseases with which the expression of SURH is associated. For example, polynucleotide sequences encoding SURH may be used in hybridization or PCR assays of fluids or tissues from biopsies to detect SURH expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The SURH nucleotide sequence disclosed herein provides the basis for assays that detect activation or induction associated with inflammation or disease. The SURH nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the Sao nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of SURH nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for SURH expression must be established. This is accomplished by combining body fluids or cell extracts taken from normal subjects, either animal or human, with SURH, or a portion thereof, under conditions suitable for hybridization or amplification. Standard hybridization may be quantified by comparing the values obtained for normal subjects with a dilution series of SURH run in the same experiment where a known amount of substantially purified SURH is used. Standard values obtained from normal samples may be compared with values obtained from samples from patients afflicted with SURH-associated diseases. Deviation between standard and subject values is used to establish the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

Polymerase Chain Reaction (PCR) as described in U.S. Pat. Nos. 4,683,195 and 4,965,188 provides additional uses for oligonucleotides based upon the SURH sequence. Such oligomers are generally chemically synthesized, but they may be generated enzymatically or produced from a recombinant source. Oligomers generally comprise two nucleotide sequences, one with sense orientation (5'→3') and one with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods which may be used to quantitate the expression of a particular molecule include radiolabeling (Melby P C et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or calorimetric response gives rapid quantitation. A definitive diagnosis of this type may allow health professionals to begin aggressive treatment and prevent further worsening of the condition. Similarly, further as-says can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutic Use

Based upon its homology to the genes encoding SURs and its expression profile, the SURH polynucleotide disclosed herein may provide the basis for the design of molecules for the treatment of diseases such as NIDDM, PHHI, and other diseases associated with the SUR and/or the $K_{ATP}$ channel.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense SURH. See, for example, the techniques described in Sambrook et al (supra) and Ausubel et al (supra).

The polynucleotides comprising full length cDNA sequence and/or its regulatory elements enable researchers to use SURH as an investigative tool in sense (Youssoufian H and HF Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding SURH can be turned off by transfecting a cell or tissue with expression vectors which express high levels of a desired SURH nucleotide fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of SURH, ie, the promoters, enhancers, and introns. Oligonucleotides derived from the transcription initiation site, eg, between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al (In: Huber B E and B I Carr (1994) *Molecular and Immunologic Approaches*, Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of RNA encoding SURH.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding SURH. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and DA vivo therapy. For ex vivo therapy, vectors are introduced into stem cells taken from the patient and clonally propagated for autologous transplant back into that same patient as presented in U.S. Pat. Nos. 5,399,493 and 5,437,994, disclosed herein by reference. Delivery by transfection and by liposome are quite well known in the art.

Furthermore, the nucleotide sequences for SURH disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for SURH can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask B J (1991; Trends Genet 7:149–54).

The technique of fluorescent in situ hybridization of chromosome spreads has been described, among other places, in Verma et al (1988) *Human Chromosomes: a Manual of Basic Techniques*, Pergamon Press, New York N.Y. Fluorescent a situ hybridization of chromosomal preparations and other physical chromosome mapping techniques may be correlated with additional genetic map data. Examples of genetic map data can be found in the 1994 Genome Issue of Science (265:1981f). Correlation between the location of a SURH on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers may be used for extending genetic maps. For example, an STS based map of the human genome was recently published by the Whitehead-MIT Center for Genomic Research (Hudson T J et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to llq22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks'solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture and Storage

The pharmaceutical compositions of the present invention may be manufactured in a manner that is known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. S-alts tend to be more soluble in aqueous or other protonic solvents that are the corresponding free base forms. In other cases, the preferred preparation may be a lyophilized powder in 1 mM-50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition. For administration of SURH, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration.

Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

The examples below are provided to illustrate the subject invention and are not included for the purpose of limiting the invention.

EXAMPLES

I CDNA Library Construction

The BRAINOT03 cDNA library was constructed from normal brain tissue removed from a 26 year old male. The frozen tissue was homogenized and lysed using a Brinkmann Homogenizer Polytron PT-3000 (Brinkmann Instruments, Westbury N.J.). The reagents and extraction procedures were used as supplied in the Stratagene RNA Isolation Kit (Cat. # 200345; Stratagene). The lysate was centrifuged over a 5.7 M CsCl cushion using a Beckman SW28 rotor in a Beckman L8–70M Ultracentrifuge (Beckman Instruments) for 18 hours at 25,000 rpm at ambient temperature. The RNA was extracted once with phenol chloroform pH 8.0, once with acid phenol pH 4.0, precipitated using 0.3 M sodium acetate and 2.5 volumes of ethanol, resuspended in water and DNase treated for 15 min at 37° C. The RNA was isolated using the OLIGOTEX kit (QIAGEN Inc, Chatsworth Calif.) and used to construct the cDNA library.

The RNA was handled according to the recommended protocols in the SuperScript Plasmid System for cDNA Synthesis and Plasmid Cloning (Cat. #18248-013; Gibco/BRL). cDNAs were fractionated on a Sepharose CL4B column (Cat. #275105, Pharmacia), and those cDNAs exceeding 400 bp were ligated into PSPORT 1. The plasmid PSPORT 1 was subsequently transformed into DH5a competent cells (Cat. #18258-012, Gibco/BRL).

II Isolation and Sequencing of CDNA Clones

Plasmid DNA was released from the cells and purified using the Miniprep Kit (Cat. # 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. # 22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 $\mu$l of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200; MJ Research, Watertown Mass.) and Applied Biosystems 377 DNA Sequencing Systems (Perkin Elmer), and reading frame was determined.

III Homology Searching of CDNA Clones and Their Deduced Proteins

Each cDNA was compared to sequences in GenBank using a search algorithm developed by Applied Biosystems and incorporated into the INHERIT 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish-regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al. supra).

Analogous computer techniques use BLAST (Altschul SF 1993 and 1990, supra) to search for identical or related molecules in nucleotide databases such as GenBank or the LIFESEQ™ database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of the search are reported as a list of libraries in which the SURH encoding sequence occurs. Abundance and percentage abundance of the SURH encoding sequence are also reported. Abundance directly reflects the number of times a particular transcript is represented in a cDNA library, and percent abundance is abundance divided by the total number of sequences examined in the cDNA library.

V Extension of SURH to Full Length or to Recover Regulatory Elements

The nucleic acid sequence encoding SURH (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known SURH nucleotide sequence "outward", generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK(QIAGEN Inc). After recovery of the DNA, Klenow enzyme was used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 µl of liquid LB/2×Carb medium placed in an individual well of an appropriate, commercially-available, sterile 96-well -microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer and one or both of the gene specific primers used for the extension reaction are added to each well. Amplification is performed using the following conditions:

| | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |

| | |
|---|---|
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of [$\gamma$-$^{32}$P] adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NENT).

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The nucleotide sequence encoding SURH, or any part thereof, is used to inhibit in vivo or in vitro expression of naturally occurring SURH. Although use of antisense oligonucleotides, comprising about 20 base-pairs, is specifically described, essentially the same procedure is used with larger cDNA fragments. An oligpnucleotide based on the coding sequence of SURH as shown in FIGS 1A–1G is used to inhibit expression of naturally occurring SURH. The complementary oligonucleotide is designed from the most unique 5' sequence as shown in FIGS 1A–1G and used either to inhibit transcription by preventing promoter binding to the upstream nontranslated sequence or translation of a SURH transcript by preventing the ribosome from binding. Using an appropriate portion of the leader and 5' sequence of SEQ ID NO:2, an effective antisense oligonucleotide includes any 15–20 nucleotides spanning the region which translates into thee signal or early coding sequence of the polypeptide as shown in FIGS. 1A–1G.

VIII Expression of SURH

Expression of SURH may be accomplished by subcloning the cDNAs into appropriate expression vectors and transfecting the vectors into analogous expression hosts. In this case, the cloning vector, PSPORT 2, previously used for the generation of the cDNA library also provides for direct expression of SURH sequences in E coli. Upstream of the cloning site, this vector contains a promoter for 8-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods will produce a fusion protein corresponding to the first seven residues of β-galactosidase, about 15 residues of "linker", and the peptide encoded within the cDNA. Since cDNA clone inserts are generated by an essentially random process, there is one chance in three that the included cDNA will lie in the correct frame for proper translation. If the cDNA is not in the proper reading frame, it can be obtained by deletion or insertion of the appropriate number of bases by well known methods including in vitro mutagenesis, digestion with exonuclease III or mung bean nuclease, or the inclusion of an oligonucleotide linker of appropriate length.

The SURH cDNA can be shuttled into other vectors known to be useful for expression of protein in specific hosts. Oligonucleotide primers containing cloning sites as well as a segment of DNA (about 25 bases) sufficient to hybridize to stretches at-both ends of the target cDNA can be synthesized chemically by standard methods. These primers can then used to amplify the desired gene segment by PCR. The resulting gene segment can be digested with appropriate restriction enzymes under standard conditions and isolated by gel electrophoresis. Alternately, similar gene segments can be produced by digestion of the cDNA with appropriate restriction enzymes. Using appropriate primers, segments of coding sequence from more than one gene can be ligated together and cloned in appropriate vectors. It is possible to optimize expression by construction of such chimeric sequences.

Suitable expression hosts for such chimeric molecules include, but are not limited to, mammalian cells such as Chinese Hamster Ovary (CHO) and human 293 cells, insect cells such as Sf9 cells, yeast cells such as *Saccharomyces cerevisiae*, and bacteria such as *E. coli*. For each of these cell systems, a useful expression vector may also include an origin of replication to allow propagation in bacteria and a selectable marker such as the β-lactamase antibiotic resistance gene to allow plasmid selection in bacteria. In addition, the vector may include a second selectable marker such as the neomycin phosphotransferase gene to allow selection in transfected eukaryotic host cells. Vectors for use in eukaryotic expression hosts may require RNA processing elements such as 3' polyadenylation sequences if such are not part of the cDNA of interest.

Additionally, the vector may contain promoters or enhancers which increase gene expression. Such promoters are host specific and include MMTV, SV40, and metallothionine promoters for CHO cells; trp, lac, tac and T7 promoters for bacterial hosts; and alpha factor, alcohol oxidase and PGH promoters for yeast. Transcription enhancers, such as the rous sarcoma virus enhancer, may be used in mammalian host cells. Homogeneous cultures of recombinant cells are obtained through standard culture methods. Cellular fractions from cells containing SURH are prepared by solubilization of the whole cell and isolation of subcellular fractions by differential centrifugation, by the addition of detergent, or by other methods well known in the art. These fractions can be used directly in the following assay.

IX SURH Activity

The SU binding activity of SURH or biologically active fragments thereof may be assayed in a competitive binding assay. The competitive binding of 5-[$^{25}$I]iodo-2-hydroxyglyburide ($^{125}$I-HGB; Nelson et al (1992) J Biol Chem 267:14928–14933) and an unlabeled SU to SURH is measured by subsequent UV-crosslinking of bound $^{125}$I-HGB to the protein. Detergent-solubilized or membrane-bound SURH, or soluble fragments of SURH, are incubated with varying concentrations of unlabeled SU plus a predetermined concentration of $^{125}$I-HGB until equilibrium is reached. Aliquots are irradiated at 312 nm to cross-link SURH-bound $^{125}$I-HGB to the protein. The irradiated protein samples are electrophoresed on SDS-polyacrylamide gels. The gels are dried and subjected to autoradiography. Bands corresponding to $^{125}$I-labeled SURH are excised from the dried gels, and the radioactivity quantitated in a gamma radiation counter. Data obtained using different concentrations of unlabeled SUs are used to calculate values for the number, affinity, and association of SURH with the candidate SU ligands using an equation such as presented in Nelson et al (supra).

X Production of SURH Specific Antibodies

SURH substantially purified using PAGE electrophoresis (Sambrook, supra) is used to immunize rabbits and to produce antibodies using standard protocols. The amino acid sequence translated from SURH is analyzed using DNASTAR software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions is described by Ausubel F M et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel F M et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring SURH Using Specific Antibodies

Naturally occurring or recombinant SURH is substantially purified by immunoaffinity chromatography using antibodies specific for SURH. An immunoaffinity column is constructed by covalently coupling SURH antibody to an activated chromatographic resin such as CnBr-activated Sepharose (Pharmacia Biotech). After the coupling, the resin is blocked and washed according to the manufacturer's instructions.

Cellular fractions from cells containing SURH are prepared by solubilization of the whole cell and isolation of subcellular fractions by differential centrifugation, by the addition of detergent, or by other methods well known in the art.

A fractionated SURH-containing preparation is passed over the immunoaffinity column, and the column is washed under conditions that allow the preferential absorbance of SURH (eg, high ionic strength buffers in the presence of detergent). The column is eluted under conditions that disrupt antibody/SURH binding (eg, a buffer of pH 2–3 or a high concentration of a chaotrope such as urea or thiocyanate ion), and SURH is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising an amino acid sequence of SEQ ID NO:1 or a fragment of SEQ ID NO:1 from amino acid residue S913 to R960.

2. A method for using a polypeptide to screen a plurality of other molecules for a molecule which specifically binds the polypeptide, the method comprising:
   a) combining the polypeptide of claim 1 with the plurality of molecules under conditions suitable to allow complex formation, and
   b) detecting complex formation, wherein the presence of the complex identifies a molecule which specifically binds the polypeptide.

3. A method of using a polypeptide to purify a molecule or compound which specifically binds the polypeptide from a sample, the method comprising:
   a) combining the polypeptide of claim 1 with a sample under conditions to allow specific binding;
   b) recovering the bound polypeptide; and
   c) separating the polypeptide from the molecule or compound, thereby obtaining purified molecule or compound.

4. A pharmaceutical composition comprising a polypeptide of SEQ ID NO:1 in conjunction with a pharmaceutically acceptable excipient.

5. A method of making a polyclonal antibody comprising:
   a) immunizing an animal with a polypeptide comprising residues S913 to R960 of SEQ ID NO: 1 under conditions to elicit an antibody response;
   b) isolating animal antibodies; and
   c) screening the isolated antibodies with the polypeptide thereby identifying a polyclonal antibody that binds specifically to the polypeptide.

6. A method of making a monoclonal antibody comprising:
   a) immunizing an animal with a polypeptide comprising residues S913 to R960 of SEQ ID NO: 1 under conditions to elicit an antibody response;
   b) isolating antibody-producing cells from the animal;
   c) fusing the antibody-producing cells with immortalized cells in culture to form monoclonal antibody-producing hybridoma cells;
   d) culturing the hybridoma cells; and
   e) isolating from the culture monoclonal antibodies which bind specifically to the polypeptide.

* * * * *